(12) United States Patent
Li et al.

(10) Patent No.: US 9,457,008 B2
(45) Date of Patent: *Oct. 4, 2016

(54) JOINT PRODUCT COMPRISING SYNEPHRINE AND TOPIRAMATE

(71) Applicant: Institute of Pharmacology and Toxicology Academy of Military Medical Sciences P.L.A. China, Beijing (CN)

(72) Inventors: Song Li, Beijing (CN); Chunsheng Gao, Beijing (CN); Wu Zhong, Beijing (CN); Yuli Wang, Beijing (CN); Meiyan Yang, Beijing (CN); Li Shan, Beijing (CN); Xinbo Zhou, Beijing (CN); Zhibing Zheng, Beijing (CN); Xiaokui Wang, Beijing (CN)

(73) Assignee: Institute of Pharmacology and Toxicology Academy of Military Medical Sciences P.L.A. China, Beijing (CN)

( * ) Notice: Subject to any disclaimer, the term of this patent is extended or adjusted under 35 U.S.C. 154(b) by 0 days.

This patent is subject to a terminal disclaimer.

(21) Appl. No.: 14/386,478

(22) PCT Filed: Mar. 22, 2013

(86) PCT No.: PCT/CN2013/073024
§ 371 (c)(1),
(2) Date: Sep. 19, 2014

(87) PCT Pub. No.: WO2013/139292
PCT Pub. Date: Sep. 26, 2013

(65) Prior Publication Data
US 2015/0056292 A1 Feb. 26, 2015

(30) Foreign Application Priority Data
Mar. 23, 2012 (CN) .......................... 2012 1 0086529

(51) Int. Cl.
*A61K 9/50* (2006.01)
*A61K 31/357* (2006.01)
(Continued)

(52) U.S. Cl.
CPC .......... *A61K 31/357* (2013.01); *A61K 9/1676* (2013.01); *A61K 9/5078* (2013.01);
(Continued)

(58) Field of Classification Search
None
See application file for complete search history.

(56) References Cited

U.S. PATENT DOCUMENTS 8,663,683 B2 * 3/2014 Liang ................... A61K 9/1676
424/458
2002/0064563 A1 5/2002 Thakur et al.
(Continued)

FOREIGN PATENT DOCUMENTS

CN 1646538 A 7/2005
CN 1905857 A 1/2007
(Continued)

OTHER PUBLICATIONS

International Search Report (ISR) for PCT/CN2013/073024; I.A. fd: Mar. 22, 2013, mailed Jul. 11, 2013 from the State Intellectual Property Office of the P.R. China, Beijing, China.
(Continued)

*Primary Examiner* — Robert A Wax
*Assistant Examiner* — Melissa Mercier
(74) *Attorney, Agent, or Firm* — Sterne, Kessler, Goldstein & Fox P.L.L.C.

(57) ABSTRACT

The present invention provides a joint product comprising synephrine and topiramate, in which the synephrine or salt thereof is administered in form of rapid-release preparation, preferably rapid-release pellet, having daily dose of 2 mg to 25 mg, preferably 5 mg to 20 mg; the topiramate is administered in form of sustained-release or controlled-release preparation, preferably sustained-release pellet, having daily dose of 20 mg to 100 mg, preferably 23 mg to 92 mg. The composition is used for treatment of obesity or other diseases associated with obesity.

25 Claims, 3 Drawing Sheets

(51) Int. Cl.
| | |
|---|---|
| *A61K 31/137* | (2006.01) |
| *A61K 9/16* | (2006.01) |
| *A61K 31/7048* | (2006.01) |
| *A61K 45/06* | (2006.01) |

(52) U.S. Cl.
CPC .......... *A61K 9/5084* (2013.01); *A61K 9/5089* (2013.01); *A61K 31/137* (2013.01); *A61K 31/7048* (2013.01); *A61K 45/06* (2013.01); *A61K 9/1635* (2013.01); *A61K 9/1652* (2013.01); *A61K 9/5026* (2013.01); *A61K 9/5047* (2013.01)

(56) References Cited

U.S. PATENT DOCUMENTS

| | | | |
|---|---|---|---|
| 2003/0072802 A1 | 4/2003 | Cutler | |
| 2005/0191351 A1* | 9/2005 | Kidane et al. | 424/468 |
| 2005/0250944 A1* | 11/2005 | Chen | C07C 67/14 544/170 |
| 2007/0154550 A1* | 7/2007 | Arti | A61K 9/1676 424/472 |
| 2008/0118557 A1 | 5/2008 | Liang et al. | |
| 2009/0304789 A1 | 12/2009 | Najarian et al. | |
| 2010/0215739 A1 | 8/2010 | Najarian et al. | |
| 2011/0207718 A1 | 8/2011 | Bird | |
| 2011/0287103 A1 | 11/2011 | Liang et al. | |
| 2015/0044295 A1 | 2/2015 | Li et al. | |
| 2015/0099003 A1 | 4/2015 | Li et al. | |

FOREIGN PATENT DOCUMENTS

| | | |
|---|---|---|
| CN | 1988889 A | 6/2007 |
| CN | 101035519 A | 9/2007 |
| CN | 101291662 A | 10/2008 |
| CN | 101862297 A | 10/2010 |
| CN | 102112126 A | 6/2011 |
| CN | 102112127 A | 6/2011 |
| CN | 102170874 A | 8/2011 |
| CN | 102579367 A | 7/2012 |
| CN | 1419444 A | 5/2013 |
| JP | 2001-321126 A | 11/2001 |
| WO | WO 99/44581 A2 | 9/1999 |
| WO | WO 03/070738 A2 | 8/2003 |
| WO | WO 2005/048981 A1 | 6/2005 |
| WO | WO 2005/079748 A2 | 9/2005 |
| WO | WO 2006/009403 A1 | 1/2006 |
| WO | WO 2006/017537 A1 | 2/2006 |
| WO | WO 2007/048027 A2 | 4/2007 |
| WO | WO 2007/102714 A1 | 9/2007 |
| WO | WO 2008/027557 A2 | 3/2008 |
| WO | WO 2008/048469 A2 | 4/2008 |
| WO | WO 2009/152189 A1 | 12/2009 |
| WO | WO 2009/152190 A1 | 12/2009 |
| WO | WO 2010/015029 A1 | 2/2010 |
| WO | WO 2011/095973 A1 | 8/2011 |
| WO | WO 2011/107855 A2 | 9/2011 |
| WO | WO 2013/139209 A1 | 9/2013 |
| WO | WO 2013/139266 A1 | 9/2013 |
| WO | WO 2013/139292 A1 | 9/2013 |

OTHER PUBLICATIONS

International Preliminary Report on Patentability (IPRP), Chapter I of the Patent Cooperation Treaty, including the Written Opinion for PCT/CN2013/073024; I.A. fd: Mar. 22, 2013, issued Sep. 23, 2014, from the International Bureau of WIPO, Geneva, Switzerland.
Clapham, JC et al., "Anti-obesity drugs: a critical review of current therapies and future opportunities," Pharmacol Ther, Jan. 2001; 89(1): 81-121, Pergamon Press, Oxford, England.
Rossato, LG et al.,"Synephrine: from trace concentrations to massive consumption in weight-loss," Food Chem Toxicol, Jan. 2011; 49(1): 8-16, Elsevier Science Ltd, Exeter, England.
Office Action mailed May 22, 2015 in U.S. Appl. No. 14/386,173, Li, S., et al., § 371(c) date: Sep. 18, 2014.
Drugs.com, "Povidone K30," http://www.drugs.com/inactive/providone-k30-373.html, last accessed on Jun. 17, 2015, 4 pages.
Bowen, P., "Particle Size Distribution Measurement from Millimeters to Nanometers and from Rods to Platelets," *Journal of Dispersion Science and Technology* 23(5):631-662, Marcel Dekker, Inc., United States (2002).
Office Action mailed Sep. 18, 2015 in U.S. Appl. No. 14/386,173, Li, S., et al., § 371(c) date: Sep. 18, 2014.
Office Action mailed Jul. 2, 2015 in U.S. Appl. No. 14/386,148, Li, S., et al., § 371(c) date: Sep. 18, 2014.
Ansel, H.C., et al., *Pharmaceutical Dosage Forms and Drug Delivery Systems*, 7th Ed., pp. 211, 223, 224, and 232-233, Lippincott Williams & Wilkins, United States (1999).
Office Action mailed Nov. 17, 2015 in U.S. Appl. No. 14/386,148, Li, S., et al., § 371(c) date: Sep. 18, 2014.
Office Action mailed Feb. 25, 2016 in U.S. Appl. No. 14/386,148, Li et al., §371(c) date: Sep. 18, 2014.
Applicant Initiated Interview Summary mailed Feb. 26, 2016 in U.S. Appl. No. 14/386,173, Li, S., et al., § 371(c) date: Sep. 18, 2014.
Advisory Action mailed Jan. 15, 2016 in U.S. Appl. No. 14/386,173, Li, S., et al., § 371(c) date: Sep. 18, 2014.
English language machine translation of Japanese patent application publication No. JP2001-321126A (listed on the accompanying form PTO/SB/08A as FP32, published on Nov. 20, 2001), Japan Platform for Patent Information, JPLATPAT.
Office Action mailed Apr. 26, 2016 in U.S. Appl. No. 14/386,173, Li, S., et al., §371(c) date: Sep. 18, 2014.

* cited by examiner

JOINT PRODUCT COMPRISING SYNEPHRINE AND TOPIRAMATE

TECHNICAL FIELD

The present invention relates to a joint product comprising synephrine and topiramate, especially relates to a joint product comprising a rapid-release synephrine hydrochloride and sustained-release topiramate.

BACKGROUND ART

Obesity refers to excess accumulation and/or abnormal distribution of fat in body, increased body mass, and is a multifactorial chronic metabolic disease, and incidence of obesity increases year by year due to genetic factors, reduction of physical activity and so on. Obesity as a universal endocrine metabolic disease not only is a worldwide epidemic disease threating human health, but also is closely associated with hyperlipemia, hypertension, diabetes, coronary heart disease and so on (H E Ren, et al., Drug therapy of obesity and advance thereof, Strait Pharmaceutical Journal, 2011, 23(1):88-90). Thus, it is very important to perform prevention and treatment of obesity. At present, means for prevention and treatment of obesity mainly include dietary therapy, sports therapy, drug therapy and surgery. For patients with mild obesity, diet control and sports are effective; but for patients with moderate or more serious obesity, weight loss is a long term procedure, dietary and sports therapy alone usually could not solve the problem, and drug therapy is necessary in such situations.

At present, drug for prevention and treatment of obesity are mainly appetite suppressants, especially central appetite suppressants, such as amphetamine, amfepramone, synephrine, fenfluramine, sibutramine as well as fluoxetine among antidepressants, and lipase inhibitor orlistat (trade name: Xenical). However, the above drugs all have adverse reaction or toxic and side effects in different extents, such as cardiovascular system dysfunction, cardiac valves dysfunction, arrhythmia, pulmonary hypertension, respiratory system dysfunction, etc.

Synephrine hydrochloride (1-(4-hydroxyphenyl)-2-(methylamino)-ethanol hydrochloride, also called as deoxyepinephrine) (Formula I) has been recorded in the pharmacopeias of three countries of northern Europe and Pharmacopoeia Germanica, and is an epinephrine a-receptor stimulant having certain simulation effects on heart receptor. Synephrine has effects of constricting blood vessels and raising blood pressure, as well as effects of expanding trachea and bronchia, and is used in clinic for treatment of bronchial asthma, hypotension during operation and anesthetization, collapse and shock, postural hypotension. In addition, synephrine can enhance metabolism, increase heat exhaustion, and elevate energy level and oxidation of fat, so that synephrine is also often used as an effective ingredient of weight-loss medicines. Since ephedra plants are forbidden by Food and Drug Administration (FDA) of US in 2004, synephrine is used as a substitute for ephedra plants by dietary supplement manufacturers. It has been reported that when synephrine or ephedrine was administered simultaneously with caffeine and other stimulants, adverse reactions such as dizziness, shivering, headache, arrhythmia, epilepsy, mental diseases, heart diseases and stroke may occur.

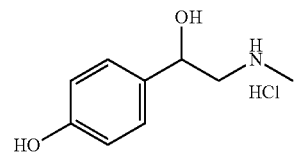

Formula 1

Topiramate (2,3,4,5-bis-O-(1-methylethylene)-β-D-fructopyranose sulfamate) (Formula 2) is a broad spectrum nerve therapeutic agent approved by FDA in 1995, and has been used in clinic for many years for treatment of some epileptic seizures and prevention of migraine headache (E. Faught, et al., (1996) Neurology 46:1684-1690), and many documents disclosed the good therapeutic effects of topiramate in treatment of diabetes (U.S. Pat. No. 7,109,174B2 and U.S. Pat. No. 6,362,220B1), dysneuria (U.S. Pat. No. 6,908,902B2), depression (U.S. Pat. No. 6,627,653B2), mental disorders (U.S. Pat. No. 6,620,819B2), headache (U.S. Pat. No. 6,319,903B1) and hypertension (U.S. Pat. No. 6,201,010B1).

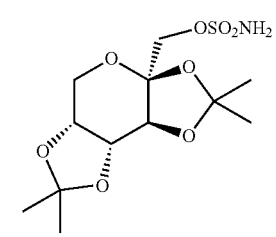

Formula 2

CONTENTS OF THE INVENTION

With immense amounts of research, we surprisingly found the combination use of synephrine or salt thereof and topiramate could effectively treat obesity with less adverse reactions and high safety.

The first aspect of the present invention relates to a joint product, comprising synephrine or salt thereof, and topiramate, optionally, further comprising a pharmaceutically acceptable adjuvant, preferably, the salt of synephrine is synephrine hydrochloride.

The second aspect of the present invention relates to a method for weight loss or for treatment of obesity or other diseases associated with obesity, the method comprising administering an individual in need of such treatment with a combination of synephrine or salt thereof and topiramate.

In an embodiment, the synephrine or salt thereof and topiramate are simultaneously or separately administered to the individual in need of such treatment; or the synephrine or salt thereof is administered first, then the topiramate is administered after an interval of time; or topiramate is administered first, then synephrine or salt thereof is administered after an interval of time, preferably, the interval of time is 0-24 h, further preferably, the interval of time is 0-18 h, more preferably, the interval of time is 0-12 h, more further preferably, the interval of time is 0-6 h, and most preferably, the interval of time is 0.1-3 h.

The third aspect of the present invention relates to a use of synephrine or salt thereof and topiramate in combination in manufacture of a medicament for weight loss, or in combination in manufacture of a medicament for treatment of obesity or other diseases associated with obesity.

In an embodiment of the present invention, as for the joint product of the first aspect or the treatment method or weight loss method of the second aspect or the use of the third aspect of the present invention, wherein the synephrine or salt thereof is a rapid-release oral solid preparation, preferably a rapid-release preparation, more preferably a rapid-release pellet; the topiramate is a sustained-release or controlled-release oral solid preparation, preferably a sustained-release preparation, more preferably a sustained-release pellet.

Preferably, the sustained-release pellet of topiramate consists of the following 3 parts: a) a blank pellet core; b) an active drug layer, the drug layer not comprising a binding agent; c) a sustained-release coating layer, in which the active drug layer is located on surface of the blank pellet core, and the sustained-release coating layer covers the external surface of the active drug layer;

preferably, the sustained-release coating layer comprises a sustained-release coating material (including but not being limited to ethyl cellulose, Eudragit NE 30D, Eudragit RS 30D, or Eudragit RL30D, preferably ethyl cellulose and Eudragit NE 30D, most preferably ethyl cellulose);

preferably, the sustained-release coating layer further comprises a plasticizer (including but not being limited to glycerol, propylene glycol, polyethylene glycol, glycerol triacetate, triethyl citrate, phthalates or dibutyl sebate, preferably glycerol triacetate), a pore-forming agent (including but not being limited to polyethylene glycols, povidone, sucrose, salts, hydroxypropyl methyl cellulose, hydroxypropyl methyl cellulose, preferably povidone (PVP K30)), an anti-sticking agent (including but not being limited to talc powder, magnesium stearate, aerosil, preferably talc powder), a coloring agent (including but not being limited to iron oxide yellow, iron oxide red, Coccinellin, lemon yellow, sunset yellow, indigo blue, etc.), a light-screening agent (including but not being limited to titanium dioxide, etc.), a flavoring agent (including but not being limited to mint essence, lemon essence, orange essence, eucalyptol, caryophyllene alcohol, etc.), a sweetening agent (including but not being limited to aspartame, vanillin, sorbitol, mannitol, artificial essences, etc.);

further preferably, the sustained coating layer comprises ethyl cellulose and povidone K30;

further more preferably, the usage amount ratio of ethyl cellulose to PVP K30 is 1:0.20-1:0.45, preferably 1:0.25-1:0.40, particularly preferably 1:0.3-1:0.35; more further preferably, the weight increment range of the sustained-release coating layer is 5% to 15%, preferably 5% to 8%, more preferably 6% to 8%;

preferably, the rapid-release pellet of synephrine or salt thereof comprises active drug synephrine or salt thereof, a filling agent (including but not being limited to microcrystalline cellulose, lactose, sucrose, etc.), and a binding agent (including but not being limited to starch slurry, syrup, polyvinylpyrrolidone (povidone, PVP, such as PVP K30), methyl cellulose (MC), ethyl cellulose (EC), highly-substituted hydroxypropyl cellulose (H-HPC), hydroxypropyl methyl cellulose (HPMC), sodium carboxymethyl cellulose, gelatin, Arabic gum, sodium alginate, etc.);

preferably, the rapid-release pellet of synephrine or salt thereof consists of 2 parts: a) a blank pellet core; b) an active drug layer, in which the active drug layer is located on the surface of the blank pellet core;

preferably, the blank pellet core has a particle diameters of 150 μm-1500 μm, preferably 300 μm-1000 μm, more preferably 400 μm-850 μm, most preferably 610 μm-750 μm.

In one embodiment of the present invention, as for the joint product of the first aspect or the treatment method of the second aspect of the present invention, the daily dose of synephrine or salt thereof is 2 mg to 25 mg, preferably 5 mg to 20 mg; the daily dose of topiramate is 20 mg to 100 mg, preferably 23 mg to 92 mg.

Preferably, the daily dose of synephrine or salt thereof is 5 mg, 10 mg or 20 mg, and the daily dose of topiramate is 23 mg, 46 mg or 92 mg.

In one embodiment of the present invention, as for the joint product of the first aspect or the use of the second aspect of the present invention, the product or medicament is in dosage form of capsules, tablets or granules.

The forth aspect of the present invention relates to a sustained-release pellet, consisting of the following 3 parts: a) a blank pellet core; b) an active drug layer, the active drug layer not comprising a binding agent; and c) a sustained-release coating layer, wherein, the active drug layer is located on the surface of the blank pellet core, the sustained-release coating layer covers the external surface of the active drug layer, preferably, the active drug is topiramate.

The fifth aspect of the present invention relates to a method for preparing a sustained-release pellet, the method comprising:

a) providing an active drug to perform drug-loading and coating a blank pellet core to obtain a drug-loaded pellet;

b) coating the drug-loaded pellet obtained in step a) with a sustained-release coating layer;

preferably, the active drug is topiramate;

preferably the active drug layer further comprises other pharmaceutically acceptable adjuvants;

preferably, the active drug and optional adjuvants of step a) is added with a drug solution dissolved with a suitable amount of solvent and dissolved to obtain a drug solution, and the blank pellet core is coated with the obtained drug solution;

preferably, in step b), a sustained-release coating material and other adjuvants of the sustained-release coating layer are dissolved in a solvent, and used for sustained-release coating the drug-loaded pellet obtained in step a);

preferably, the solvent is water, ethanol, acetone, propylene glycol, chloroform or a mixture thereof, preferably a mixture of water and ethanol, further preferably 50%-95% ethanol water solution (for example, can be 50% ethanol water solution, 70% ethanol water solution, 95% ethanol water solution).

Most preferably, the preparation method comprises the following steps:

a) providing topiramate and optional other adjuvants, adding with a suitable amount of solvent, heating and dissolving under stirring, providing a blank pellet core and placing in a fluidized bed coating pan for one-step pelletization, performing drug-loading and coating with the above drug solution under stirring;

b) dissolving a sustained-release coating material and other adjuvants of sustained-release coating layer in a solvent, heating and dissolving under stirring, mixing homogeneously, passing through a sieve, to obtain a sustained-release coating solution;

c) taking the drug-loaded pellet, spraying the sustained-release coating solution on the surface of the drug-loaded pellet in a fluidized bed, to obtain a sustained-release pellet of topiramate.

In the present invention, the term "joint product" refers to a product in which synephrine or salt thereof and topiramate are used in combination, the joint product can be a pharmaceutical composition consisting of synephrine or salt thereof and topiramate as two active ingredients, or two pharmaceutical compositions separately prepared with synephrine or salt thereof and topiramate. Preferably, the two pharmaceutical compositions are separately: a rapid-release oral solid preparation comprising synephrine or salt thereof, preferably rapid-release preparation, more preferably rapid-release pellet; and a sustained-release or controlled-release oral solid preparation comprising topiramate, preferably sustained-release preparation, more preferably sustained-release pellet. In the joint product, the synephrine or salt thereof and topiramate are simultaneously or separately administered to the individual in need of such treatment; or synephrine is administered firstly, then topiramate is administered after an interval of time; or topiramate is administered firstly, then synephrine or salt thereof is administered after an interval of time.

In one embodiment of the present invention, synephrine or salt thereof and topiramate are used in combination to form a compound preparation, oral administration once per day, for treatment of obesity.

In a preferable embodiment of the present invention, synephrine or salt thereof and topiramate are used in combination to form a compound preparation, oral administration once per day, for treatment of obesity, in which synephrine or salt thereof is in form of rapid-release administration and has a daily administration dose of 2 mg to 25 mg; and topiramate is in form of sustained-release or controlled-release administration, and has daily administration dose of 20 mg to 100 mg.

In a preferable embodiment of the present invention, synephrine or salt thereof and topiramate are used in combination to form a compound preparation, oral administration once per day, for treatment of obesity, in which synephrine or salt thereof is in form of rapid-release administration and has a daily administration dose of 5 mg to 20 mg; and topiramate is in form of sustained-release or controlled-release administration, and has daily administration dose of 23 mg to 92 mg.

In a more preferable embodiment of the present invention, synephrine or salt thereof and topiramate are used in combination to form a compound preparation, oral administration once per day, for treatment of obesity, in which synephrine or salt thereof is in form of rapid-release administration and has a daily administration dose of 5 mg; and topiramate is in form of sustained-release or controlled-release administration, and has daily administration dose of 23 mg.

In a more preferable embodiment of the present invention, synephrine or salt thereof and topiramate are used in combination to form a compound preparation, oral administration once per day, for treatment of obesity, in which synephrine or salt thereof is in form of rapid-release administration and has a daily administration dose of 10 mg; and topiramate is in form of sustained-release or controlled-release administration, and has daily administration dose of 46 mg.

In a more preferable embodiment of the present invention, synephrine or salt thereof and topiramate are used in combination to form a compound preparation, oral administration once per day, for treatment of obesity, in which synephrine or salt thereof is in form of rapid-release administration and has a daily administration dose of 20 mg; and topiramate is in form of sustained-release or controlled-release administration, and has daily administration dose of 92 mg.

In a more preferable embodiment of the present invention, synephrine or salt thereof and topiramate are used in combination to form a compound preparation, oral administration once per day, for treatment of obesity, in which the form for rapid-release administration of synephrine or salt thereof in is rapid-release pellet, and has a daily administration dose of 5 mg; and the form of sustained-release or controlled-release administration of topiramate is sustained-release pellet, and has daily administration dose of 23 mg.

In the composition of the present invention, the form of sustained-release or controlled-release administration of topiramate has an in vitro release rate of not greater than 35% of labelled amount within 1 h, between 30% and 60% of labelled amount within 4 h, between 60% and 90% of labelled amount within 8 h, and not less than 90% of labelled amount within in 16 h; preferably, not greater than 25% of labelled amount within 1 h, between 35% and 55% of labelled amount within 4 h, between 60% and 85% of labelled amount within 8 h, and not less than 90% of labelled amount within in 16 h; most preferably, not greater than 25% of labelled amount within 1 h, between 35% and 55% of labelled amount within 4 h, between 65% and 85% of labelled amount within 8 h, and not less than 90% of labelled amount within in 16 h.

In the joint product of the present invention, as for the form of rapid-release administration of synephrine or salt thereof, the synephrine or salt thereof as main drug can be rapidly and completely dissolved out after oral administration, in vitro dissolution rate is at least 80% of labelled amount within 60 min; preferably, the dissolution rate is at least 80% of labelled amount within 30 min; and most preferably, the dissolution rate is at least 80% of labelled amount within 5 min.

In the unit preparation of the joint product of the present invention, the content of topiramate can be 1 mg-500 mg, the content of synephrine hydrochloride can be 1 mg-40 mg; preferably, the content of topiramate is 5 mg-300 mg, the content of synephrine hydrochloride is 2 mg-35 mg; more preferably, the content of topiramate is 10 mg-250 mg, the content of synephrine hydrochloride is 3 mg-30 mg; more preferably, the content of topiramate is 20 mg-100 mg, the content of synephrine hydrochloride is 4 mg-25 mg; the most optimal content of topiramate is 23 mg-92 mg, and the content of synephrine hydrochloride is 5 mg-20 mg.

In one embodiment of the present invention, unit preparation comprises 23 mg of topiramate, 5 mg of synephrine hydrochloride; in another embodiment, unit preparation comprises 46 mg of topiramate, 10 mg of synephrine hydrochloride; in further another embodiment, unit preparation comprises 92 mg of topiramate, and 20 mg of synephrine hydrochloride.

Moreover, the present invention further provides a joint product comprising synephrine or salt thereof and sustained-release topiramate, which is a pellet preparation, the preparation comprises rapid-release pellet of synephrine and sustained-release pellet of topiramate, in which the sustained-release pellet of topiramate consists of the following 3 parts: a) a blank pellet core; b) a drug layer, the drug layer not comprising a binding agent; c) a sustained-release coating layer, in which the active drug layer is located on the surface of the blank pellet core, and the sustained-release coating layer covers the external surface of the active drug layer. In comparison with the prior art, the sustained-release pellet of topiramate does not comprise a binding agent in the drug layer, has excellent sustained-release effect, simple prescription, easy operation, stable quality, good controllability and repeatability.

In the joint product of the present invention, the blank pellet core is a pellet without physiological activity, includes but is not limited to sugar pellets, microcrystalline cellulose pellets, starch pellets, or silicon dioxide pellets; preferably sugar pellets. The blank pellet core has a particle diameters of 150 μm-1500 μm, preferably 300 μm-1000 μm, more preferably 400 μm-850 μm, most preferably 610 μm-750 μm. The blank pellet core can be commercially available, or prepared by conventional means such as extrusion spheronization method, fluidized bed method well known in the prior art.

In the joint product of the present invention, the active drug layer in the sustained-release pellet of topiramate does not comprise a binding agent, in which the binding agent includes starch slurry, syrup, polyvinylpyrrolidone (povidone, PVP, such as PVP K30), methyl cellulose (MC), ethyl cellulose (EC), highly-substituted hydroxypropyl cellulose (H-HPC), hydroxypropyl methyl cellulose (HPMC), sodium carboxymethyl cellulose, gelatin, Arabic gum, sodium alginate, etc. When a blank pellet core is loaded with drug without using a binding agent, the time for loading drug is short, the adhesion degree of pellets is low, and when direct contact between topiramate and binding agent is avoided, the stability of topiramate increases significantly.

In the joint product of the present invention, the sustained-release coating layer in the sustained-release pellet comprises a sustained-release coating material, including but not being limited to ethyl cellulose, Eudragit NE 30D, Eudragit RS 30D, or Eudragit RL30D or a mixture thereof, preferably ethyl cellulose and Eudragit NE 30D, most preferably ethyl cellulose. The coating layer can further comprises a plasticizer, a pore-forming agent, an anti-sticking agent, a coloring agent, a light-screening agent, a flavoring agent, a sweetening agent, etc., in which the plasticizer includes but is not limited to glycerol, propylene glycol, polyethylene glycol, glycerol triacetate, triethyl citrate, phthalates or dibutyl sebate or a mixture thereof, preferably glycerol triacetate; the pore-forming agent includes but is not limited to polyethylene glycols, povidone, sucrose, salts, hydroxypropyl methyl cellulose, hydroxypropyl methyl cellulose or a mixture thereof, preferably povidone (PVP K30); the anti-sticking agent includes but is not limited to talc powder, magnesium stearate, aerosil, preferably talc powder; the light-screening agent includes but is not limited to titanium dioxide, etc.; the coloring agent includes but is not limited to iron oxide yellow, iron oxide red, Coccinellin, lemon yellow, sunset yellow, indigo blue, etc.; the flavoring agent includes but is not limited to mint essence, lemon essence, orange essence, eucalyptol, caryophyllene alcohol, etc.; and the sweetening agent includes but is not limited to aspartame, vanillin, sorbitol, mannitol, artificial essences, or a mixture thereof.

In the joint product of the present invention, the sustained-release coating in the sustained-release pellet of topiramate has a weight increment range that can be determined by tests, and generally, the weight increment range of the sustained-release coating is 2%-30%, preferably 3%-20%, more preferably 4%-15%, most preferably 5%-10%.

In the sustained-release pellet of topiramate comprised in the joint product of the present invention, the active ingredients are in an amount of 10%-50%, preferably 15%-45%, more preferably 20%-40%, relative to the total weight of composition. The amount of active ingredients in unit preparation can be 0.1 mg-500 mg, preferably 1 mg-300 mg, more preferably 10 mg-250 mg, most preferably 10 mg-50 mg, most optimal 23 mg.

Further, the applicants found, after a plenty of experiments, that the above topiramate-carried pellet using the sustained-release coating layer comprising ethyl cellulose and PVP K30 in combination brought about unexpected good effects. That is, the topiramate pellet prepared with ethyl cellulose and pore-forming agent PVP K30 as sustained-release coating layer material has better stability in drug release, which ensures consistency of drug release in different batches of samples, and the expected sustained-release effect can be achieved without heat treatment after coating. Thus, the coating process is simplified, and effects of heat treatment after coating are eliminated. Wherein the usage amount ratio of ethyl cellulose to PVP K30 is 1:0.20-1:0.45, preferably 1:0.25-1:0.40, especially preferably 1:0.3-1:0.35.

In a preferable embodiment of the present invention, the drug layer of sustained-release pellet of topiramate contains topiramate, the sustained-release coating layer uses ethyl cellulose as sustained-release coating material, PVP K30 as pore forming agent, and the usage amount ratio of ethyl cellulose to PVP K30 is 1:0.20-1:0.45.

In another preferable embodiment of the present invention, the drug layer of sustained-release pellet of topiramate contains topiramate, the sustained-release coating layer uses ethyl cellulose as sustained-release coating material, PVP K30 as pore forming agent, the usage amount ratio of ethyl cellulose to PVP K30 is 1:0.20-1:0.45, and the range of weight increment of sustained-release coating is 5%-15%.

In another preferable embodiment of the present invention, the blank pellet core is sugar pellet, the drug layer of sustained-release pellet of topiramate contains topiramate, the sustained-release coating layer uses ethyl cellulose as sustained-release coating material, PVP K30 as pore forming agent, the usage amount ratio of ethyl cellulose to PVP K30 is 1:0.25-1:0.40, and the range of weight increment of sustained-release coating is 5%-15%.

In further another preferable embodiment of the present invention, the blank pellet core is sugar pellet having a particle diameters of 610 μm-750 μm, the drug layer of sustained-release pellet of topiramate contains topiramate, the sustained-release coating layer uses ethyl cellulose as sustained-release coating material, PVP K30 as pore forming agent, the usage amount ratio of ethyl cellulose to PVP K30 is 1:0.25-1:0.40, and the range of weight increment of sustained-release coating is 5%-10%.

In further another preferable embodiment of the present invention, the blank pellet core is sugar pellet having a particle diameters of 610 μm-750 μm, the drug layer of sustained-release pellet of topiramate uses topiramate as active drug, the sustained-release coating layer uses ethyl cellulose as sustained-release coating material, PVP K30 as pore forming agent, the usage amount ratio of ethyl cellulose to PVP K30 is 1:0.25-1:0.40, and the range of weight increment of sustained-release coating is 5%-8%.

In an particular embodiment of the present invention, the blank pellet core is sugar pellet having a particle diameters of 610 μm-750 μm, the drug layer of sustained-release pellet of topiramate contains topiramate, the sustained-release coating layer uses ethyl cellulose as sustained-release coating material, PVP K30 as pore forming agent, the usage amount ratio of ethyl cellulose to PVP K30 is 1:0.3-1:0.35, and the range of weight increment of sustained-release coating is 6%-8%.

In the present invention and the above embodiments, the drug layer of sustained-release pellet of topiramate contains topiramate, and further contains other pharmaceutically acceptable adjuvants, such as surfactants, disintegrating agents, flavoring agents, sweetening agents, anti-sticking agents, light-screening agents, etc. The surfactants include anionic surfactants, cationic surfactant, zwitterionic surfactants, and non-ionic surfactants, including but not being limited to sodium dodecyl sulfate, sodium hexadecanol sulfate, sodium octadecanol sulfate, sodium dodecyl benzene sulfate, sodium dioctyl sulfosuccinate, dihexyl sulfosuccinate, lecithin, sorbitan fatty acid esters, polyoxyethylene sorbitan fatty acid esters, polyoxyethylene fatty acid esters, polyoxyethylene fatty alcohol ethers, polymer of ethylene oxide and propylene oxide, polyoxyethylene 40 monostearate, polyoxyethylene 50 stearate, oxirane triblock copolymer, epoxypropane triblock copolymer, sorbitan monopalmitate (Span-40), sorbitan monostearate (Span-60), glyceryl monostearate, polyoxyethylene stearate, or mixtures thereof; the disintegrating agents include but are not limited to microcrystalline cellulose, low-substituted hydroxypropyl cellulose sodium, crosslinked polyvinylpyrrolidone, sodium carboxymethyl starch, pre-gelatinized starch, alginic acid, starch, effervescing disintegrants, or mixtures thereof; the anti-sticking agents include but are not limited to talc powder, magnesium stearate, aerosil, preferably talc powder; the light-screening agents include but are not limited to titanium dioxide, etc.; the flavoring agents include but are not limited to mint essence, lemon essence, orange essence, eucalyptol, caryophyllene alcohol, etc.; the sweetening agents include but are not limited to aspartame, vanillin, sorbitol, mannitol, artificial essences, etc. Preferably, the drug layer merely contains topiramate as active drug.

The sustained-release pellet of topiramate of the present invention can bring about good therapeutic effect by once administration per 24 h, the in vivo blood concentration of drug is stable, peak concentration decreases significantly, and good sustained-release effect is achieved. The sustained-release pellet of topiramate of the present invention has in vitro release rate of: not greater than 35% within 1 h, between 30% and 60% within 4 h, between 60% and 90% within 8 h, and not less than 90% within in 16 h; preferably, not greater than 25% within 1 h, between 35% and 55% within 4 h, between 60% and 85% within 8 h, and not less than 90% within in 16 h; most preferably, not greater than 25% within 1 h, between 35% and 55% within 4 h, between 65% and 85% within 8 h, and not less than 90% within in 16 h.

The preferable conditions for determining the release rate in the present invention are in accordance with the first method (for sustained-release preparation or controlled-release preparation) of Release Rate Measurement (Appendix X D) of Part II of Chinese Pharmacopoeia, 2010 Edition, using apparatus as stated in the second method (slurry method) of Dissolution Rate Measurement (Appendix X C) of Part II of Chinese Pharmacopoeia, 2010 Edition, in which samples are taken and analyzed at different specified time points by using water (500 ml) as releasing media, at 37° C. and rotation speed of 100 rpm.

On the other hand, the present invention further provides a method for preparing a sustained-release pharmaceutical composition of topiramate, the method comprising:

a) providing ingredients of drug layer to perform drug-loading and coating a blank pellet core;

b) subjecting the drug-loaded pellet to sustained-release coating.

Preferably, the method for preparing a sustained-release pellet of topiramate comprises the following steps:

a) providing topiramate and other adjuvants of drug layer, adding with a suitable amount of solvent for dissolution, and performing drug-loading and coating a blank pellet core;

b) subjecting the drug-loaded pellet to sustained-release coating.

More preferably, the method for preparing a sustained-release pellet of topiramate comprises the following steps:

a) providing topiramate and other adjuvants of drug layer, adding with a suitable amount of solvent for dissolution, and performing drug-loading and coating a blank pellet core with the drug solution;

b) dissolving a sustained-release coating material and other adjuvants of sustained-release coating layer in a solvent, subjecting the drug-loaded pellet to sustained-release coating.

Most preferably, the method for preparing a sustained-release pellet of topiramate comprises the following steps:

a) providing topiramate and other adjuvants of drug layer, adding with a suitable amount of solvent, heating and dissolving under stirring, providing a blank pellet core and placing in a fluidized bed coating pan for one-step pelletization, performing drug-loading and coating with the above drug solution under stirring;

b) dissolving a sustained-release coating material and other adjuvants of sustained-release coating layer in a solvent, heating and dissolving under stirring, mixing homogeneously, passing through a 100 mesh sieve, to obtain a sustained-release coating solution;

c) taking the drug-loaded pellet, spraying the sustained-release coating solution on the surface of the drug-loaded pellet in a fluidized bed, to obtain a sustained-release pellet of topiramate.

The suitable solvent for the method of the present invention is water, ethanol, acetone, propylene glycol, chloroform or a mixture thereof, preferably a mixture of water and ethanol, further preferably 50%-95% ethanol water solution (for example, can be 50% ethanol water solution, 70% ethanol water solution, 95% ethanol water solution).

In the method for preparing sustained-release pellet of topiramate of the present invention, the active ingredient in drug layer is topiramate, the drug layer does not contain a binding agent, in which the binding agent refers to starch slurry, syrup, polyvinylpyrrolidone (povidone), methyl cellulose, ethyl cellulose, highly-substituted hydroxypropyl cellulose, hydroxypropyl methyl cellulose, sodium carboxymethyl cellulose, gelatin, Arabic gum, sodium alginate, etc. The drug layer can further comprises other pharmaceutically acceptable adjuvants, such as surfactants, disintegrating agents, flavoring agents, sweetening agents, anti-sticking agents, light-screening agents, etc. The surfactant include anionic surfactants, cationic surfactant, zwitterionic surfactants, and non-ionic surfactants, including but not being limited to sodium dodecyl sulfate, sodium hexadecanol sulfate, sodium octadecanol sulfate, sodium dodecyl benzene sulfate, sodium dioctyl sulfosuccinate, dihexyl sulfosuccinate, lecithin, sorbitan fatty acid esters, polyoxyethylene sorbitan fatty acid esters, polyoxyethylene fatty acid esters, polyoxyethylene fatty alcohol ethers, polymer of ethylene oxide and propylene oxide, polyoxyethylene 40 monostearate, polyoxyethylene 50 stearate, oxirane triblock copolymer, epoxypropane triblock copolymer, sorbitan monopalmitate (Span-40), sorbitan monostearate (Span-60), glyceryl monostearate, polyoxyethylene stearate, or mixtures thereof; the disintegrating agents include but are not limited to microcrystalline cellulose, low-substituted hydroxypropyl cellulose sodium, crosslinked polyvinylpyrrolidone, sodium carboxymethyl starch, pregelatinized starch, alginic acid, starch, effervescing disintegrants, or mixtures thereof; the anti-sticking agents include but are not limited to talc powder, magnesium stearate, aerosil, preferably talc powder; the light-screening agents include but are not limited to titanium dioxide, etc.; the flavoring agents include but are not limited to mint essence, lemon essence, orange essence, eucalyptol, caryophyllene alcohol, etc.; the sweetening agents include but are not limited to aspartame, vanillin, sorbitol, mannitol, artificial essences, etc. Most preferably, the drug layer merely contains topiramate as active drug.

In the method for preparing sustained-release pellet of topiramate of the present invention, the sustained-release coating material in the sustained-release coating layer includes but is not limited to ethyl cellulose, Eudragit NE 30D, Eudragit RS 30D, or Eudragit RL30D, preferably ethyl cellulose and Eudragit NE 30D, most preferably ethyl cellulose. The sustained-release coating layer further comprises a plasticizer, a pore-forming agent, an anti-sticking agent, a coloring agent, a light-screening agent, a flavoring agent, a sweetening agent, etc., in which the plasticizer includes but is not limited to glycerol, propylene glycol, polyethylene glycol, glycerol triacetate, triethyl citrate, phthalates or dibutyl sebate, preferably glycerol triacetate; the pore-forming agent includes but is not limited to polyethylene glycols, povidone, sucrose, salts, hydroxypropyl methyl cellulose, hydroxypropyl methyl cellulose, preferably povidone (PVP K30); the anti-sticking agent includes but is not limited to talc powder, magnesium stearate, aerosil, preferably talc powder; the light-screening agent includes but is not limited to titanium dioxide, etc.; the coloring agent includes but is not limited to iron oxide yellow, iron oxide red, Coccinellin, lemon yellow, sunset yellow, indigo blue, etc.; the flavoring agent includes but is not limited to mint essence, lemon essence, orange essence, eucalyptol, caryophyllene alcohol, etc.; and the sweetening agent includes but is not limited to aspartame, vanillin, sorbitol, mannitol, artificial essences, etc.

Preferably, the sustained-release coating layer of the sustained-release pellet of topiramate of the present invention contains ethyl cellulose and PVP K30.

In a specific embodiment of the present invention, the method for preparing pellet of topiramate comprises:

a) Topiramate is provided as main drug, dissolved with ethanol solution to prepare a solution with concentration of 20% (w/v) for drug-loading and coating. A blank pellet core is provided and placed in a fluidized bed coating pan for one step pelletization, and the above drug solution is used for drug-loading and coating under stirring to obtain a drug-loaded pellet core.

b) Ethyl cellulose as sustained-release coating material is dissolved in an ethanol solution to achieve a concentration of 3-8% (w/v), preferably 5-7% (w/v), and added with a suitable amount of specific pore-forming agent, PVP K30, then heated and dissolved under stirring, stirred homogenously, after passing through 100 mesh sieve, it is atomized and sprayed on the drug-loaded pellet core with active drug layer of topiramate in a fluidized bed bottom-spraying coating pan to perform sustained-release coating.

The process parameters for drug-loading and sustained-release coating in the fluidized bed can be regulated according to practical situations, and preferable process parameters are as follows:

Drug-loading and coating—inlet air temperature is 50-70° C. (to keep pan internal temperature at 40±2° C.); inlet air pressure is 0.3-0.5 bar; atomization pressure is 1.0-2.0 bar; solution spray rate is 5-15 g/min.

Sustained-release coating—inlet air temperature is 40-45° C. (to keep pan internal temperature at 30-35° C.); inlet air pressure is 0.3-0.5 bar; atomization pressure is 1.0-2.0 bar; solution spray rate is 3-12 g/min.

In the joint product of the present invention, the pellet of synephrine or salt thereof is rapid-release pellet, which can perform rapid-release after oral administration. It can be prepared by a conventional method for preparation of pellet, such as centrifugation pelletization, extrusion spheronization, and fluidized bed drug-loading and coating method.

Specifically, the following method can be used for the preparation: 400 g of blank sucrose pellet cores is placed in a centrifugation pelletizer, synephrine or salt thereof is weighed and added to a feeder of the pelletizer, a binding agent and other adjuvants are sprayed so that drug powder is homogeneously laminated on mother cores, after the end of powder supplying, they are taken out, dried to obtain rapid-release drug-loaded pellets of synephrine or salt thereof; the following method can also be used for the preparation: synephrine or salt thereof is weighed, homogeneously mixed with a filling agent and other adjuvants, added with a binding agent to obtain a suitable soft material, the soft material is placed in a spheronizator, extruded and spheronized, the obtained pellets are dried, sieved, to obtain rapid-release pellets of synephrine or salt thereof; the following method can also be used for the preparation: synephrine or salt thereof and a suitable amount of binding agent and other adjuvants are weighed, and dissolved with a suitable solvent to obtain a drug-containing coating solution, blank pellet cores are weighed, placed in a fluidized bed bottom spray coating pan, the drug-containing coating solution is sprayed in manner of bottom spray to the surface of the blank pellet cores when the blank pellet cores are in fluidized state, the materials are continuously fluidized for 5 min after the end of drug-loaded, then taken out to obtain rapid-release drug-loaded pellets of synephrine or salt.

In the joint product of the present invention, the rapid-release pellet of synephrine or salt thereof comprises synephrine or salt thereof as active drug, a filling agent and a binding agent, the filling agent includes but is not limited to microcrystalline cellulose, lactose, sucrose, etc.; the binding agent includes but is not limited to starch slurry, syrup, polyvinylpyrrolidone (povidone, PVP, such as PVP K30), methyl cellulose (MC), ethyl cellulose (EC), highly-substituted hydroxypropyl cellulose (H-HPC), hydroxypropyl methyl cellulose (HPMC), sodium carboxymethyl cellulose, gelatin, Arabic gum, sodium alginate, etc. The pellet of synephrine can further comprise other pharmaceutically acceptable adjuvants, such as surfactants, disintegrating agents, flavoring agents, sweetening agents, anti-sticking agents, light-screening agents, plasticizers, etc. The surfactants include anionic surfactants, cationic surfactant, zwitterionic surfactants, and non-ionic surfactants, including but not being limited to sodium dodecyl sulfate, sodium hexadecanol sulfate, sodium octadecanol sulfate, sodium dodecyl benzene sulfate, sodium dioctyl sulfosuccinate, dihexyl sulfosuccinate, lecithin, sorbitan fatty acid esters, polyoxyethylene sorbitan fatty acid esters, polyoxyethylene fatty acid esters, polyoxyethylene fatty alcohol ethers, polymer of ethylene oxide and propylene oxide, polyoxyethylene 40 monostearate, polyoxyethylene 50 stearate, oxirane triblock copolymer, epoxypropane triblock copolymer, sorbitan monopalmitate (Span-40), sorbitan monostearate (Span-60), glyceryl monostearate, polyoxyethylene stearate, or mixtures thereof; the disintegrating agents include but are not limited to microcrystalline cellulose, low-substituted hydroxypropyl cellulose sodium, crosslinked polyvinylpyrrolidone, sodium carboxymethyl starch, pregelatinized starch, alginic acid, starch, effervescing disintegrants, or mixtures thereof; the anti-sticking agents include but are not limited to talc powder, magnesium stearate, aerosil, preferably talc powder; the light-screening agents include but are not limited to titanium dioxide, etc.; the flavoring agents include but are not limited to mint essence, lemon essence, orange essence, eucalyptol, caryophyllene alcohol, etc.; the sweetening agents include but are not limited to aspartame, vanillin, sorbitol, mannitol, artificial essences, etc.; the sweetening agent includes but is not limited to aspartame, vanillin, sorbitol, mannitol, artificial essences, etc.; the plasticizer includes but is not limited to glycerol, propylene glycol, polyethylene glycol, glycerol triacetate, triethyl citrate, phthalates and dibutyl sebate.

In the pellet of synephrine of the joint product of the present invention, synephrine or salt thereof as active ingredient is in an amount of 1%-30%, preferably 2%-20%, more preferably 3%-15%, relative to the total weight of the pellet of synephrine or salt thereof. The amount of active ingredients in unit preparation can be 1 mg-40 mg, preferably 2 mg-35 mg, more preferably 3 mg-30 mg, most preferably 3.5 mg-25 mg, most optimal 5 mg-20 mg.

The pellet of synephrine or salt thereof of the present invention has a dissolution rate of at least 80% of labelled amount within 30 min; preferably, the dissolution rate is at least 80% of labelled amount within 15 min; and most preferably, the dissolution rate is at least 80% of labelled amount within 5 min.

The pellets as prepared in the present invention have particle diameters of 150 μm-1500 μm, preferably 300 μm-1000 μm, more preferably 400 μm-850 μm, most preferably 610 μm-750 μm.

The pellet of synephrine or salt thereof and the pellet of topiramate in the present invention can be further processed to form various suitable preparations, for example, can be loaded in capsules to form synephrine-topiramate compound capsules, or be tableted to form tablets.

SPECIFIC MODELS FOR CARRYING OUT THE INVENTION

Figure 1:
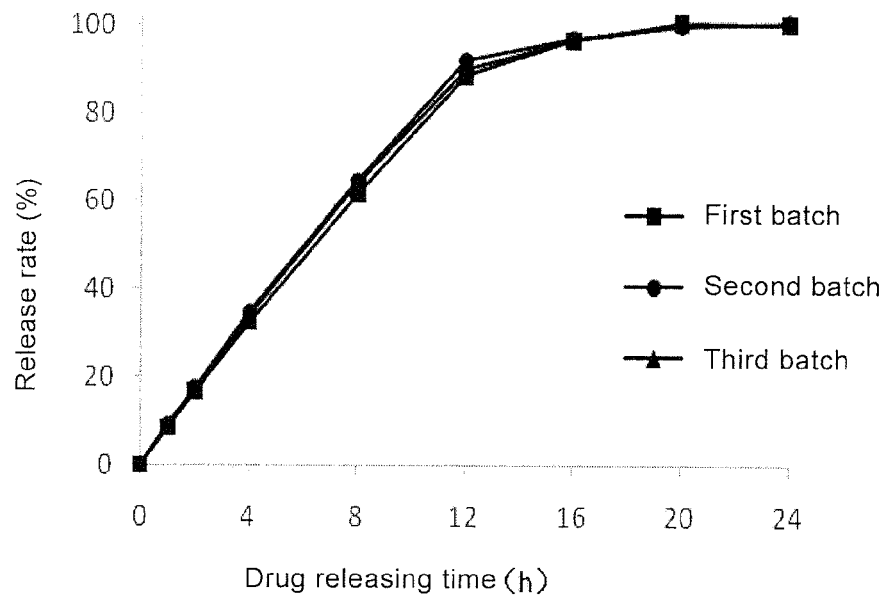
FIG. 1 shows a drug release profile of sustained-release pellet of topiramate in water.

The present invention is further illustrated with the following specific examples. It should be pointed out that the following examples are merely used to illustrate the present invention, and those skilled in the art can correspondingly change the present invention according to the technology and common knowledge in the art with the understanding of the spirit of the present invention, and all these technical solutions fall into the scope of the present invention. If specific conditions are not given in the examples, conventional conditions or conditions suggested by manufacturers are used. If manufacturers of the used reagents or instruments were not given, they were all conventional products commercially available in markets.

In the examples of the present invention, unless specifically pointed out, release rates of topiramate were all measured by the following method. According to the first method (for sustained-release preparation or controlled-release preparation) of Release Rate Measurement (Appendix X D) of Part II of Chinese Pharmacopoeia, 2010 Edition, the apparatus as stated in the second method (slurry method) of Dissolution Rate Measurement (Appendix X C) of Part II of Chinese Pharmacopoeia, 2010 Edition, was used to perform the measurement using water (500 ml) as releasing media, at 37° C. and rotation speed of 100 rpm. Samples (5 ml, supplemented with equivalent volume of media at the meantime) were taken at specified time points and filtrated, the subsequent filtrates were used as test solutions. High performance liquid chromatography (Appendix V D, Part II of Chinese Pharmacopoeia, 2010 Edition) was used, octylsilane-bonded silica gel was used as packing agent, column temperature was 35° C., 50% methanol was mobile phase, differential refractive detector was used, flow rate was 1.5 ml per minute. 200 μl of test solution was taken, injected in liquid chromatograph, the peak area of topiramate as main drug was recorded; topiramate was separately taken as control sample and measured by the same method, and accumulative release percentages of drug at different time points were calculated by external standard method.

In the examples of the present invention, unless specifically pointed out, dissolution rates of synephrine were all measured by the following method. According to the second method (slurry method) of Dissolution Rate Measurement (Appendix X C) of Part II of Chinese Pharmacopoeia, 2010 Edition, which was performed by using water (500 ml) as dissolution media, at 37° C. and rotation speed of 50 rpm, samples (5 ml, supplemented with equivalent volume of media at the meantime) were taken at specified time points and filtrated, the subsequent filtrates were used as test solutions. UV-Visible spectrophotometry (Appendix IV A, Part II of Chinese Pharmacopoeia, 2010 Edition) was used to measure absorbance at wavelength of 225 nm. Synephrine hydrochloride was separately taken as control sample, precisely weighed, added with water, dissolved and quantitatively diluted to form a solution with 0.1 mg per 1 ml, measured by the same method, and accumulative dissolution percentages of synephrine as main drug at different time points were calculated.

In the following specific models, unless specifically pointed out, the obtained parameters were all calculated according to the following formulations:

$$\text{Pellet drug-loading rate}(\%) = (W_{total\ weight\ of\ pellets} - W_{blank\ pellet\ core\ weight}) / W_{amount\ of\ bulk\ drug} \times 100\%$$

$$\text{Weight increment of sustained-release coating}(\%) = \\ (W_{total\ weight\ of\ pellets\ after\ sustained-release\ coating} - \\ W_{total\ weight\ of\ pellets\ before\ sustained-release\ coating}) / \\ W_{total\ weight\ of\ pellets\ after\ sustained-release\ coating} \times \\ 100\%$$

Adhesion rate of pellet=($W_{total\ weight\ of\ pellets\ after\ coating}$ − $W_{total\ weight\ of\ pellets\ without\ adhesion}$)/$W_{total\ weight\ of\ pellets\ after\ coating}$×100%

Example 1

Preparation of Pellets of Topiramate

| Prescription | |
|---|---|
| Topiramate | 400 g |
| Blank pellet core | 600 g |
| Ethyl cellulose | 60 g |
| Povidone (PVP K 30) | 20.25 g |

Preparation Method

Topiramate as main drug was dissolved or suspended in a suitable solvent (e.g., 75% ethanol water solution), to form a drug-loading coating solution with solid content of 30% (w/v), it was sprayed and laminated on surface of blank pellet cores (such as sucrose pellet core with particle diameter ranging from 710 to 850 μm) when the blank pellet cores were in fluidization state to form drug-loaded pellets of topiramate. Then, ethyl cellulose and Povidone (PVP K 30) were dissolved in a suitable amount of ethanol or suspended in water (e.g., 95% ethanol water solution) to form a solution as sustained-release coating solution with solid content of 10% (w/v), the pellets of topiramate were subjected to sustained-release coating to obtain sustained-release pellets of topiramate.

Example 2

Measurement of Release Rate of Sustained-Release Pellet of Topiramate

In order to verify whether the sustained-release pellet of topiramate of the present invention had desired sustained-release effect, 3 batches of sustained-release pellets of topiramate were prepared by repeating the prescription and method of Example 1, and release rates thereof were measured. An amount of sustained-release pellets of topiramate (containing about 92 mg of topiramate as main drug) was taken, and measured according to the first method (for sustained-release preparation or controlled-release preparation) of Release Rate Measurement (Appendix X D) of Part II of Chinese Pharmacopoeia, 2010 Edition, the apparatus as stated in the second method (slurry method) of Dissolution Rate Measurement (Appendix X C) of Part II of Chinese Pharmacopoeia, 2010 Edition, was used to perform the measurement using water (500 ml) as releasing media, at 37° C. and rotation speed of 100 rpm. Samples (5 ml, supplemented with equivalent volume of media at the meantime) were taken at specified time points and filtrated, the subsequent filtrates were used as test solutions. High performance liquid chromatography (Appendix V D, Part II of Chinese Pharmacopoeia, 2010 Edition) was used, octylsilane-bonded silica gel was used as packing agent, column temperature was 35° C., 50% methanol was mobile phase, differential refractive detector was used, flow rate was 1.5 ml per minute. 200 μl of test solution was taken, injected in liquid chromatograph, the peak area of topiramate as main drug was recorded; topiramate was separately taken as control sample and measured by the same method, and accumulative release percentages of drug at different time points were calculated by external standard method. The results were shown in FIG. 1, which showed that the sustained-release pellet of topiramate in the pharmaceutical composition of the present invention had significant in vitro sustained-release effects.

Example 3

Studying on In Vivo Pharmacokinetics of Sustained-Release Pellet of Topiramate Test samples: the topiramate drug-loaded pellet core (rapid-release pellet) as prepared in Example 1 was used as control preparation, and the sustained-release pellet of topiramate as prepared in Example 1 was used as test preparation. Each administration dose was 23 mg expressed in topiramate as main drug.

Test subjects: 6 Beagles, half male and half female, the body weight of Beagles was 8.97±1.05 kg.

Dosage regimen: 6 Beagles were subjected to double cycle random crossover test design, separately orally administrated once with equivalent dose of the test preparation containing 23 mg of topiramate as main drug and the control preparation containing 23 mg of topiramate as main drug, a wash-out period with interval time of 15 days was set between the two cycles. Blood samples (2 mL) were separated taken from leg veins of the Beagles at 0.5, 1, 2, 3, 4, 6, 8, 10, 12, 16, 24, 36, 48 h after administration, placed in negative pressure glass tubes treated with heparin sodium, centrifuged at 4000 r/min for 10 min to separate plasma, the plasma was moved to 1 mL EP tube, labeled with test number, random number of Beagle and blood sampling time, the blood samples were kept at −20° C. for treatment and analysis.

Plasma sample treatment: 100 μL of plasma of Beagle after administration was taken, placed in 1.5 ml centrifuge tube, added with 20 μl of water, added with 20 μl of internal standard solution (500 ng/ml Nimesulide solution), added with 0.5 ml of methanol as precipitator, subjected to eddy for 3 min, centrifuged for 10 min (9500 rpm), supernatants (20 μl) were separately sucked up, and analyzed with LC/MS/MS under the following chromatography conditions, and chromatograms were recorded.

Chromatography conditions: analysis column was Zorbax C8, 5 μm particle size, 150×4.6 mm I.D., Agilent Company of US; pre-column was C18 protection column, 4×3.0 mm I.D., Phenomenex Company, USA; column temperature was 25° C.; mobile phase was methanol-0.5 mM ammonium acetate (75:25, v/v); flow rate was 0.5 mL/min; internal standard was Nimesulide (500 ng/mL).

Mass spectrometric conditions: API 3000 type tandem quadrupole mass spectrometer. Ion source was atmospheric chemical ion source (Turbo lonspray source); detection was performed in negative ion manner; ejection voltage was −4200 V; source temperature was 450° C.; nebulizer gas (NEB) was 8; curtain gas (CUR) was 11; collision gas (CAD) was 5; scanning manner was multiple reaction monitoring (MRM), the ion reactions for quantitative analysis were separately: m/z 338→m/z 78 (topiramater, CE—55 V), m/z 307→m/z 229 (internal standard nimesulide, CE—20 V); scanning time was 150 msec.

Pharmacokinetic data treatment: blood concentration data were analyzed with DAS 2.0 analytic software.

Figure 2:
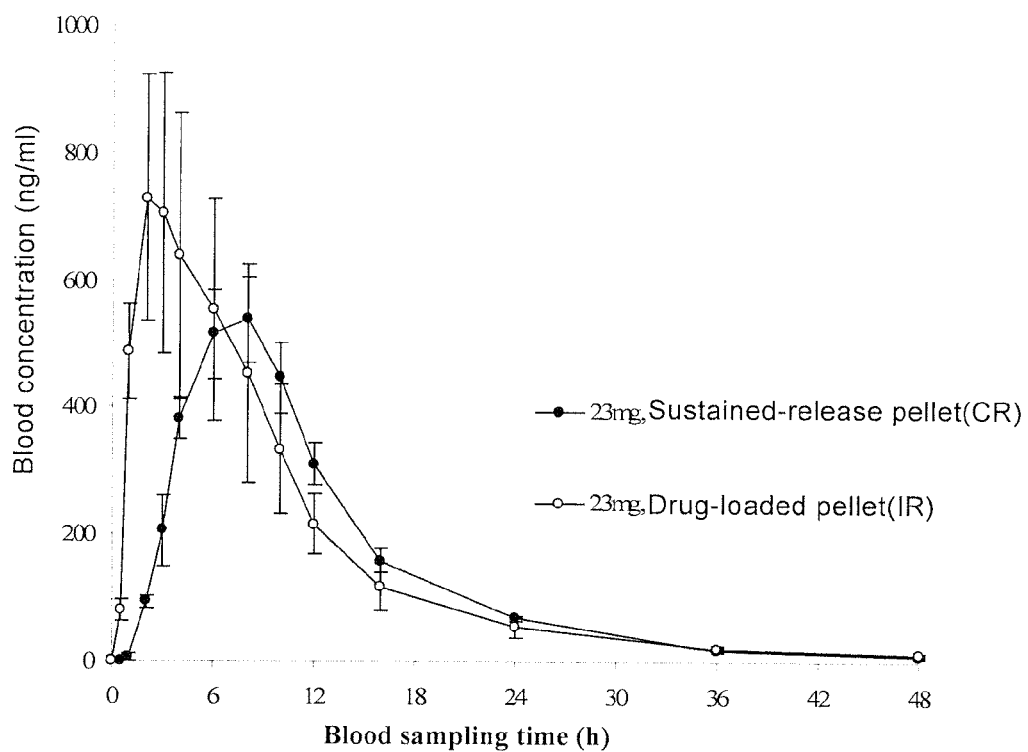
FIG. 2 shows in vivo blood concentration curve of sustained-release pellet of topiramate in Beagle.

Results of measurement: after Beagles were orally administered with equivalent dose (23 mg) of control preparation (topiramate drug-loaded pellet cores of Example 1) and test preparation (sustained-release pellet of topiramate of Example 1), average blood concentrations (μg/ml) at different time points were shown in FIG. 2, and main pharmacokinetic parameters were shown in Table 1.

TABLE 1

Main pharmacokinetic parameters

| Test sample | $T_{max}$ (h) | $C_{max}$ (µg·ml$^{-1}$) | $AUC_{0 \to Tn}$ (h·µg·ml$^{-1}$) | Relative bioavailability (%) |
|---|---|---|---|---|
| Control preparation | 2.33 ± 0.47 | 1.11 ± 0.13 | 9.39 ± 3.23 | 100.00% |
| Test preparation | 7.33 ± 0.94 | 0.55 ± 0.07 | 8.72 ± 2.67 | 92.87% |

The results of FIG. 2 and Table 1 showed that the Beagles orally administered with the sustained-release composition of topiramate as provided by the present invention (sustained-release pellets of topiramate of Example 1, containing 23 mg of topiramate) showed significantly extended Tmax, significantly decreased Cmax, in comparison with the rapid-release topiramate drug-loaded pellet cores (control preparation, topiramate pellet cores of Example 1, containing 23 mg of topiramate), and more important, the relative bioavailability of the test preparation was 92.87% of that of the control preparation. This indicated that the topiramate sustained-release composition as provided by the present invention had biologically equivalent to the control preparation, and showed significant features of sustained-release preparation, that was, the peak concentration decreased significantly, and the action time was significantly extended.

Example 4

Preparation of Rapid-Release Pellet of Synephrine

| Prescription | |
|---|---|
| Synephrine hydrochloride | 100 g |
| Blank pellet core | 500 g |
| Preparation method | |

Synephrine hydrochloride as main drug was dissolved or suspended in a suitable solvent (e.g., water), to form a drug-loading coating solution with solid content of 60% (w/v), it was sprayed and laminated on surface of blank pellet cores (such as sucrose pellet core with particle diameter ranging from 710 to 850 µm) when the blank pellet cores were in fluidization state to form rapid-release pellets of synephrine hydrochloride.

Example 5

Figure 3:
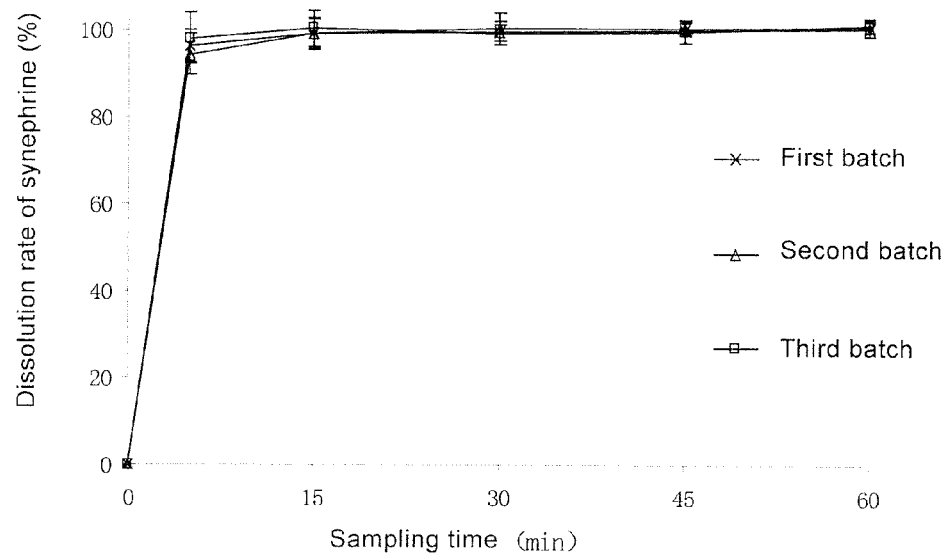
FIG. 3 shows drug dissolution profile of rapid-release pellet of synephrine in water.

Measure of In Vitro Dissolution Rate of Rapid-Release Pellet of Synephrine Hydrochloride In order to verify whether the rapid-release pellet of synephrine hydrochloride of the present invention had desired in vitro rapid-release effect, 3 batches of rapid-release pellets of synephrine hydrochloride were prepared by repeating the prescription and method of Example 4, and dissolution rates thereof were measured. An amount of rapid-release pellets of synephrine hydrochloride (containing about 20 mg of synephrine hydrochloride as main drug) was taken, and measured according to the second method of Dissolution Rate Measurement (Appendix X C, slurry method) of Part II of Chinese Pharmacopoeia, 2010 Edition, using water (500 ml) as releasing media, at 37° C. and rotation speed of 50 rpm. Samples (5 ml, supplemented with equivalent volume of media at the meantime) were taken at specified time points and filtrated, the subsequent filtrates were used as test solutions. UV-visible spectrophotometry (Appendix IV A of Chinese Pharmacopoeia, 2010 Edition), was used to measure absorbance at wavelength of 225 nm. Synephrine hydrochloride was separately taken as control sample, precisely weighed, added with water, dissolved and quantitatively diluted to form a solution with 0.04 mg per 1 ml, measured by the same method, and accumulative dissolution percentages of synephrine as main drug at different time points were calculated. The measurement results were shown in FIG. 3, and showed that the rapid-release pellet of synephrine hydrochloride in the pharmaceutical composition of the present invention had rapid in vitro dissolution rate, 90% or more of main drug was dissolved within 5 min, which showed desired in vitro rapid-release effects.

Example 6

Preparation of Sustained-Release Capsules of Compound Synephrine-Topiramate

The sustained-release pellet of topiramate prepared in Example 1 and the rapid-release pellet of synephrine prepared in Example 4 were taken, mixed homogeneously in certain weight ratio as calculated with contents, and filled in capsules so that each capsule contained 23 mg of topiramate and 5 mg of synephrine hydrochloride.

Example 7

Preparation of Sustained-Release Capsules of Compound Synephrine-Topiramate

The sustained-release pellet of topiramate prepared in Example 1 and the rapid-release pellet of synephrine prepared in Example 4 were taken, mixed homogeneously in certain weight ratio as calculated with contents, and filled in capsules so that each capsule contained 46 mg of topiramate and 10 mg of synephrine hydrochloride.

Example 8

Preparation of Sustained-Release Capsules of Compound Synephrine-Topiramate

The sustained-release pellet of topiramate prepared in Example 1 and the rapid-release pellet of synephrine prepared in Example 4 were taken, mixed homogeneously in certain weight ratio as calculated with contents, and filled in capsules so that each capsule contained 92 mg of topiramate and 20 mg of synephrine hydrochloride.

Example 9

12 volunteers with body mass index (BMI) ≥30 kg/m$^2$, half male and half female, age of 22-55, were subjected to randomization, double blind, parallel classes to compare weight loss effects of 3 preparations: capsules of rapid-release pellet of synephrine hydrochloride, capsules of sustained-release pellet of topiramate and capsules of sustained-release pellet of compound synephrine hydrochloride-topiramate (combination use of rapid-release pellet of synephrine hydrochloride and sustained-release pellet of topiramate). The capsules of rapid-release pellet of synephrine hydrochloride contained 5 mg of synephrine hydrochloride; the capsules of sustained-release pellet of topiramate contained 23 mg of topiramate; and the capsules of sustained-release pellet of compound synephrine hydrochloride-topiramate contained 5 mg of rapid-release synephrine hydrochloride and 23 mg of sustained-release topiramate. The rapid-release pellet of synephrine hydrochloride and the sustained-release pellet of topiramate were separately prepared according to the preparation methods and prescriptions of Example 1 and Example 4, and filled in capsules according to experimental requirements of dose as calculated with contents.

The observation time after administration was 24 weeks, once per day, one capsule per time. After 12 weeks, the number of capsules of administration could increase according to changes of body weight, once per day, 2-4 capsules per time. During observation, all subjects followed individual dietary of 500 kcal/day, i.e., strengthening the reduction of food intake by eating various kinds of foods of "Food Guide Pyramid" as basic specified dietary, eating more fruits and vegetables, and drinking 8 glasses of water. The subjects were required to strengthen physical exercise and increase amount of exercise.

After the end of experiment, the percentage variation of body weight of the subjects were examined. The results showed that the average (SE) estimation of weight loss of the group of capsules of sustained-release pellet of compound synephrine hydrochloride-topiramate was 5.45% (0.81%), that of the group of capsules of rapid-release pellet of synephrine hydrochloride was 2.01% (0.38%), and that of the capsules of sustained-release pellet of topiramate was 1.35% (0.65%). It could be seen that the pharmaceutical composition (capsules of sustained-release pellet of compound synephrine hydrochloride-topiramate) as provided by the present invention had exactly weight loss effects, and its weight loss effects were superior to those of single rapid-release synephrine or single sustained-release topiramate. In respect of safety, the pharmaceutical composition (capsules of sustained-release pellet of compound synephrine hydrochloride-topiramate) as provided by the present invention had not exhibited significant adverse reaction, while the group of capsules of rapid-release pellet of synephrine hydrochloride and the group of capsules of sustained-release pellet of topiramate frequently resulted in adverse reactions such as dizziness, cognitive injury and somnolence.

Example 10

A 38 aged female patient with obesity (body weight 115 kg, BMI35 kg/m2) was administrated once per day with 1 capsule of the pharmaceutical composition (capsules of sustained-release pellet of compound synephrine hydrochloride-topiramate, containing 5 mg of rapid-release synephrine and 23 mg of topiramate) as provided by the present invention, and the dose increased 2 times after 1 month, i.e., 2 capsules each time. After 3 months of treatment, her body weight reduced by 5.5 kg, and she had "full up" feel and more vigor after eating a small amount of food, without other side-effects of body. The patient reduced 15 kg of body weight without any side-effects after 12 months of combination drug therapy.

Example 11

Comparison in Drug-Loading and Coating Between Drug-Containing Solutions with and without Binding Agent Prescription

| Pre-scription | Topiramate (g) | Binding agent (g) | | | | 50% ethanol (ml) |
|---|---|---|---|---|---|---|
| | | HPMC | PVP | HPC | Free of binding agent | |
| 1 | 230 | 6.9 g | — | — | — | 1150 |
| 2 | 230 | — | 6.9 g | — | — | 1150 |
| 3 | 230 | — | — | 6.9 g | — | 1150 |
| 4 | 230 | — | — | — | — | 1150 |

Preparation method: 4 Parts of topiramate raw material were weighed, 230 g per part, separately added with suitable amount of 50% ethanol, stirred and heated at 40° C.-50° C. for dissolution; then HPMC(E5), PVP K30 and HPC, each 6.9 g, were separately weighed, added in order to the first part, the second part, and the third part, while the fourth part was free of binding agent; they were stirred and heated at 40° C.-50° C. for dissolution, then added with 50% ethanol to reach 1150 ml to obtain drug-containing coating solutions with different binding agents.

500 g of sucrose pellet cores (710-850 μm) were placed in a fluidized bed bottom spray coating pan, the inlet air temperature was set as 55° C. (to keep pan internal temperature at 40±2° C.); inlet air pressure was 0.35 bar; atomization pressure was 1.5 bar; solution spray rate was 5-15 g/min (regulated according to fluidization state at any time). The drug-containing coating solution was sprayed in manner of bottom spray on surface of sucrose pellet cores when the sucrose pellet cores were in fluidization state, after the end of drug-loading, the material was continuously fluidized at 45° C. for 5 min to obtain drug-loaded pellets with different binding agents, which were weighed, and results were shown in Table 2.

The experimental results showed that when topiramate was loaded on blank pellet cores without a binding agent, the drug-loading time was shortened, the adhesion degree of pellets decreased, and the stability of topiramate was significantly improved because direct contact between topiramate and binding agent was avoided.

TABLE 2

Results of drug-loading and coating using drug-containing solutions with and without a binding agent

| Index | Prescription 1 | Prescription 2 | Prescription 3 | Prescription 4 |
|---|---|---|---|---|
| Adhesion degree (%) | 7.8 | 3.7 | 5.5 | 2.1 |
| Drug-loading time (min) | 71 | 62 | 68 | 54 |
| Drug-loading rate of pellet(%) | 94.2 | 93.7 | 95.1 | 95.4 |

Example 12

Results of Drug-Loading and Coating Using Drug-Containing Coating Solutions with Different Solvents 4 Parts of topiramate raw material were weighed, 230 g per part, separately added with suitable amount of 50% ethanol, 70% ethanol, 95% ethanol, and anhydrous ethanol, stirred and heated at 40° C.-50° C. for dissolution; then corresponding solvent was supplemented to reach 1150 ml to obtain drug-containing coating solutions with different solvents as dissolvent.

500 g of sucrose pellet cores (710-850 μm) were placed in a fluidized bed bottom spray coating pan, the inlet air temperature was set as 55° C. (to keep pan internal temperature at 40±2° C.); inlet air pressure was 0.35 bar; atomization pressure was 1.5 bar; solution spray rate was 5-15 g/min (regulated according to fluidization state at any time). The drug-containing coating solution with different solvents as dissolvent was sprayed on surface of sucrose pellet cores in manner of bottom spray when the sucrose pellet cores were in fluidization state, after the end of drug-loading, the material was continuously fluidized at 45° C. for 5 min to obtain drug-loaded pellets with different solvents as dissolvent, which were weighed, and results were shown in Table 3. The results showed that an amount of water in solvent for drug-containing and coating facilitated drug-loading and coating. If there is no water, drug-loading rate was low and drug loss increased, although adhesion degree of pellets decreased and coating time could be shortened. When the solvent for drug-loading and coating contained water ranging from 50% to 95%, the adhesion degree of pellets and the coating time showed no significant difference, while the drug-load rate was greater than 90%, so that it was generally reasonable.

TABLE 3

Results of drug-loading and coating using drug-containing coating solutions with different solvents as dissolvent

| Index | 50% ethanol | 70% ethanol | 95% ethanol | Anhydrous ethanol |
|---|---|---|---|---|
| Adhesion degree (%) | 2.1 | 2.2 | 1.9 | 1.8 |
| Drug-loading time(min) | 54 | 50 | 48 | 44 |
| Drug-loading rate on pellet (%) | 95.4 | 94.5 | 91.6 | 90.4 |

Example 13

Comparison of Release Rates of Sustained-Release Pellets of Topiramate with Blank Pellet Cores Having Different Particle Diameters Prescription of Drug-Loaded Pellet:

| | | Blank pellet core | |
|---|---|---|---|
| Prescription | Topiramate (g) | Range of particle diameter (μm) | Weight (g) |
| 5 | 230 | 300-400 | 500 |
| 6 | 230 | 500-610 | 500 |
| 7 | 230 | 610-750 | 500 |

Prescription of Sustained-Release Coating Layer:

| Prescription | Ethyl cellulose (g) | PVP K30 (g) |
|---|---|---|
| 5 | 50 | 16.5 |
| 6 | 40 | 13.2 |
| 7 | 30 | 10.0 |

Preparation Method:

(1) 230 g of topiramate was weighed, added with a suitable amount of 50% ethanol, stirred and heated at 40-50° C. for dissolution, added 50% ethanol to reach 1150 ml to obtain a drug-containing coating solution.

300 μm-400 μm, 500 μm-610 μm, 710 μm-850 μm sucrose pellet cores were separately weighed, each 500 g, placed in a fluidized bed bottom spray coating pan, the inlet air temperature was set as 55° C. (to keep pan internal temperature at 40±2° C.); inlet air pressure was 0.35 bar; atomization pressure was 1.5 bar; solution spray rate was 5-15 g/min (regulated according to fluidization state at any time). The drug-containing coating solution was sprayed in manner of bottom spray on surface of sucrose pellet cores when the sucrose pellet cores were in fluidization state, after the end of drug-loading, the material was continuously fluidized at 45° C. for 5 min to obtain drug-loaded pellets of topiramate.

(2) The prescription amount of ethyl cellulose (EC) was weighed, added with a suitable amount of 95% ethanol for dissolution, then added with the prescription amount of PVP K30, dissolved to obtain a sustained-release coating solution.

(3) The above drug-loaded pellets of topiramate with different particle diameters were weighed, each 500 g, and separately placed in a fluidized bed bottom spray coating pan, the inlet air temperature was set as 40-45° C. (to keep pan internal temperature at 30-35° C.); inlet air pressure was 0.35 bar; atomization pressure was 1.5 bar; solution spray rate was 3-12 g/min. The sustained-release coating solutions of the 3 prescriptions were separately sprayed in manner of bottom spray on surfaces of drug-loaded pellets with different particle diameters when the drug-loaded pellets were in fluidization state, to obtain sustained-release pellets of topiramate with different particle diameters, in which the weight increments of sustained-release coating were 10.9%, 8.8% and 6.7%, respectively. According to calculation, the adhesion degrees of pellets were 2.2%, 2.1%, 1.8%, respectively.

The measurement results of drug release rates of the prepared sustained-release pellets of topiramate were shown in Table 4. The results showed that the particle size of blank pellet cores had no significant effects on the drug release rate of the sustained-release pellet of topiramate.

TABLE 4

Evaluation results of release rates of pellets with different particle diameters

| Prescription | Particle diameters of blank pellet cores | Release rate (%) | | | | | |
|---|---|---|---|---|---|---|---|
| | | 1 h | 4 h | 8 h | 12 h | 16 h | 20 h |
| 5 | 300-400 μm | 21.6 | 55.5 | 88.1 | 98.5 | 100.4 | 101.2 |
| 6 | 500-610 μm | 16.7 | 49.5 | 80.6 | 92.4 | 98.5 | 99.6 |
| 7 | 610-750 μm | 19.4 | 56.8 | 85.4 | 96.2 | 99.8 | 100.4 |

Example 14

Preparation of Sustained-Release Pellets of Topiramate Coated with Different Types of Sustained-Release Materials Prescription of Sustained-Release Coating:

| Prescription | 8 | 9 | 10 |
|---|---|---|---|
| Drug-loaded pellets | 500 g | 500 g | 500 g |
| Eudragit RS30D | 133 g (corresponding to 40 g of dry resin) | — | — |
| Eudragit NE30D | — | 167 g (corresponding to 50 g of dry resin) | — |
| Eudragit RL30D | — | — | 200 g (corresponding to 60 g of dry resin) |
| Talc powder | 20 | 25 | 30 |
| Water | 246 | 309 | 370 |

Preparation Method:

Aqueous dispersions of Eudragit RS30D, Eudragit NE 30D, Eudragit RL30D in prescription amounts were separately weighed, added with water in 1 time amount, stirred homogeneously; the talc powder in prescription amount was added to the residual water, homogenized with a high-shear homogenizer for 3 min, the obtained suspension was slowly poured into the above aqueous dispersions, stirred homogeneously, passed through 80 mesh sieve, to obtain sustained-release coating solutions.

500 g of drug-loaded pellets as prepared according to Prescription 4 of Example 11 was placed in a fluidized bed bottom spray coating pan, the inlet air temperature was set as 25-30° C. (to keep pan internal temperature at 23-25° C.); inlet air pressure was 0.35 bar; atomization pressure was 1.5 bar; solution spray rate was 3-5 g/min. The above 3 sustained-release coating solutions were separately sprayed on surface of the drug-loaded pellets in manner of bottom spray when the drug-loaded pellets were in fluidization state, to obtain 3 kinds of sustained-release pellets respectively with Eudragit RS30D, Eudragit NE 30D, and Eudragit RL30D as sustained-release coating material, and the weight increments of sustained-release coating were separately 9.7%, 11.9%, and 13.9%. The obtained sustained-release pellets of topiramate were subjected to aging and heating treatment in a high temperature oven at 40° C. for 24 h. According to calculation, the adhesion degrees of pellets were 2.8%, 2.7%, 3.0%, respectively.

The measurement results of drug release rates were shown in Table 5. The results showed that sustained-release pellets of topiramate with significant sustained-release features could be prepared using different types of Eudragit coating materials.

TABLE 5

Evaluation results of release rates of topiramate sustained-release pellets with different sustained-release coating materials

| Prescription | Release rate (%) | | | | | |
|---|---|---|---|---|---|---|
| | 1 h | 4 h | 8 h | 12 h | 16 h | 20 h |
| 8 | 19.6 | 44.6 | 70.2 | 88.3 | 97.7 | 99.7 |
| 9 | 15.5 | 34.4 | 66.3 | 77.9 | 92.2 | 94.8 |
| 10 | 16.4 | 36.5 | 68.3 | 79.4 | 95.1 | 98.5 |

Example 15

Preparation of Sustained-Release Pellets of Topiramate

Prescription of Sustained-Release Coating

| Prescription | 11 | 12 | 13 |
|---|---|---|---|
| EC | 30 g | 30 g | 30 g |
| PVP K30 | 9 g | 9.6 g | 10.5 g |

Preparation Method:

According to the amount proportions of the above prescriptions, ethyl cellulose was dissolved with a suitable amount of 95% ethanol, then separately added with proportion amounts of PVP K30 and dissolved to obtain sustained-release coating solutions.

500 g of drug-loaded pellets as prepared with the drug-containing coating solution without a binding agent of Example 11 was placed in a fluidized bed bottom spray coating pan, the inlet air temperature was set as 40-45° C. (to keep pan internal temperature at 30-35° C.); inlet air pressure was 0.35 bar; atomization pressure was 1.5 bar; solution spray rate was 3-12 g/min. The sustained-release coating solutions with different proportions of ethyl cellulose and PVP K30 (sustained-release coating prescriptions 11-13) were separately sprayed on surface of the drug-loaded pellets in manner of bottom spray when the drug-loaded pellets were in fluidization state, the weight increments of sustained-release coating were separately 6.56%, 6.65%, and 6.79%, so as to obtain sustained-release pellets of topiramate with different proportions of ethyl cellulose and PVP K30. According to calculation, the adhesion degrees of pellets were 2.3%, 2.4% and 2.1%, respectively. The measurement results of drug release rate were shown in Table 6. The results showed that the amount of PVP K30 in the sustained-release coating prescription had significant effects on the drug release rate of sustained-release pellet of topiramate, i.e., the greater the amount was, the faster the drug release rate of the preparation was. Thus, the sustained-release feature of sustained-release pellet of topiramate could be regulated with the amount of PVP K30 in the sustained-release coating prescription.

TABLE 6

Evaluation results of release rates of sustained-release pellet of topiramate as prepared according to the prescription 11-13

| Prescription | Release rate (%) | | | | | |
|---|---|---|---|---|---|---|
| | 1 h | 4 h | 8 h | 12 h | 16 h | 20 h |
| 11 | 17.4 | 36.6 | 64.3 | 82.5 | 90.7 | 95.5 |
| 12 | 21.8 | 47.6 | 76.4 | 91.3 | 95.7 | 97.8 |
| 13 | 24.2 | 51.4 | 83.8 | 99.7 | 99.6 | 100.2 |

Example 16

Experiment of Process Repeatability (1) Preparation of Drug-Loaded Pellet Cores of Topiramate without a Binding Agent 276 g of Topiramate raw material was weighed, added with a suitable amount of 70% ethanol, stirred under heating at 40-50° C., dissolved, added with 70% ethanol to reach 1380 ml, to obtain a drug-containing coating solution.

600 g of 710 μm-850 μm sucrose pellet cores was weighed and placed in a fluidized bed bottom spray coating pan, the inlet air temperature was set as 55° C. (to keep pan internal temperature at 40±2° C.); inlet air pressure was 0.35 bar; atomization pressure was 1.5 bar; solution spray rate was 5-15 g/min (regulated according to fluidization state at any time). The drug-containing coating solution was sprayed on surface of blank sucrose pellet cores in manner of bottom spray when the sucrose pellet cores were in fluidization state. After the end of drug-loading, the material was continuously fluidized at 45° C. for 5 min to obtain topiramate drug-loaded pellet cores without a binding agent, which were weighed, the total weight W of the pellets after the end of drug-loading was recorded, and the drug-loading rate and product yield of the pellets were calculated and shown in Table 7.

The results showed that the 3 batches of samples had high product yield, uniform drug release rate, and good process repeatability.

Example 17

Effects of Different Dissolution Media on Release Rate of Sustained-Release Pellet of Topiramate In order to verify whether acidic, basic solvent media would influence the release rate of the sustained-release pellets of the present invention, 0.1 mol/L HCl (pH1.2) was prepared as artificial gastric fluid, 0.2 ml/L phosphate buffer (pH6.8) was prepared as artificial intestinal fluid, and these media and water (500 ml) were used as release media, rotation speed was 100 rpm, 37° C. Samples (5 ml, supplemented with equivalent volume of media at the meantime) were taken at 1, 2, 4, 8, 12, 16, 20, 24 h, filtrated, and the

TABLE 7

Results of process repeatability of topiramate drug-loaded pellet cores without binding agent

| Sample batch | Production scale (preparation unit/batch) | Amount of the charged main drug (g/batch) | Amount of sucrose pellet cores (g/batch) | Amount of the produced drug-loaded pellet cores (g/batch) | Drug-loading rate (%) | Product yield (%) |
|---|---|---|---|---|---|---|
| 1 | 12000 | 276 | 600 | 864 | 95.7 | 98.6 |
| 2 | 12000 | 276 | 600 | 862 | 94.9 | 98.4 |
| 3 | 12000 | 276 | 600 | 863 | 95.3 | 98.5 |

Notation: the dose of topiramate of each preparation unit was expressed as 23 mg; the product yield was calculated by dividing the amount of drug-loaded pellet cores by the total amount of the charged raw materials and adjuvants.

(2) Preparation of Sustained-Release Coating Pellet of Topiramate 48 g of Ethyl cellulose was weighed, added with a suitable amount of 95% ethanol, stirred under heating at 40° C.-50° C., dissolved, then added with about 16.2 g of PVP K30, stirred under heating at 40° C.-50° C., dissolved, stirred homogenously, added with 95% ethanol to reach 1152 ml, to obtain a sustained-release coating solution.

Figure 4:
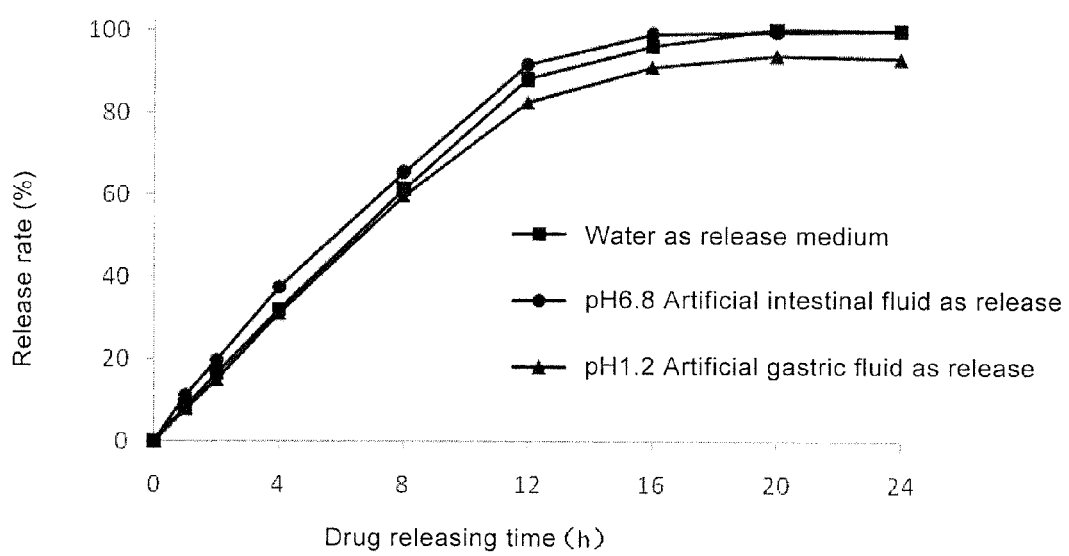
FIG. 4 shows release profiles of first batch of sustained-release coating pellet of topiramate of Example 16 in different releasing media.

800 g of drug-loaded pellets as above prepared was placed in a fluidized bed bottom spray coating pan, the inlet air temperature was set as 40-45° C. (to keep pan internal temperature at 30-35° C.); inlet air pressure was 0.35 bar; atomization pressure was 1.5 bar; solution spray rate was 3-12 g/min. The sustained-release coating solution was sprayed on surface of the drug-loaded pellets in manner of bottom spray when the drug-loaded pellets were in fluidization state, to obtain 3 batches of sustained-release pellets of topiramate, their weight increments of sustained-release coating were separately 6.87%, 6.98%, and 7.08%. According to calculation, the adhesion degrees of pellets were 2.1%, 2.0% and 2.1%, respectively. The results were shown in Table 8.

subsequent filtrates were used as test solutions. High performance liquid chromatography (Appendix V D, Part II of Chinese Pharmacopoeia, 2010 Edition) was used, octylsilane-bonded silica gel was used as packing agent, 50% methanol was mobile phase, differential refractive detector was used, flow rate was 1.5 ml per minute. 200 μl of test solution was taken, injected in liquid chromatograph, the peak area of topiramate as main drug was recorded; topiramate was separately taken as control sample and measured by the same method, and accumulative release percentages of drug at different time points were calculated by external standard method. The release profile of sample of Batch 1 in Example 16 (2) in the above media were drawn, and the results were shown in FIG. 4. The results showed that the drug release profiles of the sustained-release pellet of topiramate in the artificial gastric fluid, water and the artificial intestinal fluid were substantially consistent (since topiramate was unstable in pH1.2 artificial gastric fluid and had degradation reaction, the release rate in the artificial gastric fluid in the present experiment was derived from the sum of main drug topiramate and degradation products), which suggested that the product could release drug consistently in

TABLE 8

Experimental results of process repeatability of sustained-release coating pellets of topiramate

| Sample batch | Product amount (preparation unit/batch) | Amount of drug-loaded pellet cores, g/batch | Amount of ethyl cellulose, g/batch | Amount of PVP K30, g/batch | Sustained-release pellet of topiramate, g/batch | Product yield (%) | Release rate (%) | | | |
|---|---|---|---|---|---|---|---|---|---|---|
| | | | | | | | 1 h | 4 h | 8 h | 16 h |
| Batch 1 | 10000 | 800 | 48 | 16.2 | 859 | 99.3 | 14.4 | 37.2 | 68.5 | 96.4 |
| Batch 2 | 10000 | 800 | 48 | 16.2 | 860 | 99.5 | 15.1 | 38.6 | 69.5 | 96.8 |
| Batch 3 | 10000 | 800 | 48 | 16.2 | 861 | 99.6 | 15.9 | 39.1 | 68.8 | 96.4 | different sites of gastrointestinal tract, so as to ensure stable pharmacological effects of topiramate as active ingredient.

Example 18

Figure 5:
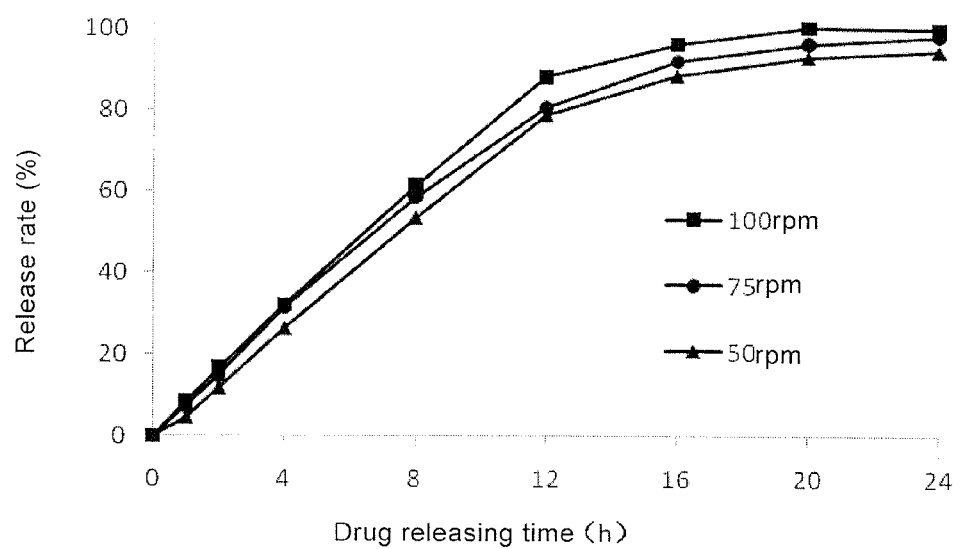
FIG. 5 shows release profiles of first batch of sustained-release coating pellet of topiramate of Example 16 under different rotation speeds.

Effects of Different Rotation Speeds on Release Rate of Sustained-Release Pellet of Topiramate In order to verify whether gastrointestinal motility would influence the release rate of the sustained-release pellets of the present invention, rotation speed was set as 50 rpm, 75 rpm and 100 rpm, respectively, and water (500 ml) were used as release media, 37° C. Samples (5 ml, supplemented with equivalent volume of media at the meantime) were taken at 1, 2, 4, 8, 12, 16, 20, 24 h, filtrated, and the subsequent filtrates were used as test solutions. High performance liquid chromatography (Appendix V D, Part II of Chinese Pharmacopoeia, 2010 Edition) was used, octylsilane-bonded silica gel was used as packing agent, 50% methanol was mobile phase, differential refractive detector was used, flow rate was 1.5 ml per minute. 200 µl of test solution was taken, injected in liquid chromatograph, the peak area of topiramate as main drug was recorded; topiramate was separately taken as control sample and measured by the same method, and accumulative release percentages of drug at different time points were calculated by external standard method. The release profile of sample of Batch 1 in Example 16 (2) under the above different rotation speeds were drawn, and the results were shown in FIG. 5. The results showed that the drug release profiles of the sustained-release pellet of topiramate under rotation speed ranging 50-100 rpm were substantially consistent, which suggested that the product could release drug consistently under different situations of gastrointestinal motility, so as to ensure stable pharmacological effects of topiramate as active ingredient.

Example 19

Studying on Drug Release Consistency

The prescriptions 8-10 were repeated 3 times according to the method of Example 14, and their drug release consistency was considered. The results were shown in Table 9. The results showed that the sustained-release prescriptions of topiramate as provided by the present invention had good drug release consistency.

TABLE 9

Results of drug release consistency of sustained-release pellet of topiramate (mean ± standard deviation)

| Prescription | Drug release rate at different time points (%) (mean ± standard deviation) | | | | |
|---|---|---|---|---|---|
| | 1 h | 4 h | 8 h | 16 h | 20 h |
| Prescription 8 | 19.6 ± 8.7 | 51.2 ± 8.3 | 75.2 ± 9.8 | 93.3 ± 9.1 | 95.7 ± 5.2 |
| Prescription 9 | 15.1 ± 7.1 | 38.8 ± 7.4 | 68.7 ± 8.7 | 92.9 ± 9.8 | 95.3 ± 4.1 |
| Prescription 10 | 14.4 ± 8.8 | 36.5 ± 8.3 | 65.3 ± 9.6 | 92.4 ± 8.1 | 95.1 ± 5.2 |
| Example 1 | 14.4 ± 2.5 | 37.2 ± 1.8 | 68.5 ± 1.4 | 96.4 ± 1.2 | 100.2 ± 0.9 |

Example 20

Prescription

| | Drug layer | | | |
|---|---|---|---|---|
| Prescription | Topiramate (g) | Sodium dodecyl sulfate (g) | Tween 80 (g) | Talc powder (g) |
| 14 | 230 | 3.45 | — | — |
| 15 | 230 | — | 6.90 | — |
| 16 | 230 | — | — | 11.5 |

| Sustained release layer | |
|---|---|
| Name | Amount |
| EC (g) | 30 |
| PVP K30 (g) | 10.0 |
| Aerosil (g) | 3.0 |
| 95% ethanol (ml) | 720 |

Preparation Method:

(1) The ingredients of drug layer in the above prescription amounts were weighed, added with a suitable amount of 50% ethanol, stirred under heating at 40° C.-50° C., dissolved (prescriptions 14 and 15) or suspended (prescription 16), added with 50% ethanol to reach 1150 ml, to obtain drug-containing coating solutions (prescriptions 14, 15) or suspension (prescription 16).

500 g of 610 µm-750 µm sucrose pellet cores was weighed and placed in a fluidized bed bottom spray coating pan, the inlet air temperature was set as 55° C. (to keep pan internal temperature at 40±2° C.); inlet air pressure was 0.35 bar; atomization pressure was 1.5 bar; solution spray rate was 5-15 g/min (regulated according to fluidization state at any time). The drug-containing coating solutions or suspension were sprayed on surface of blank pellet cores in manner of bottom spray when the sucrose pellet cores were in fluidization state. After the end of drug-loading, the material was continuously fluidized at 45° C. for 5 min to obtain topiramate drug-loaded pellets.

(2) Ethyl cellulose (EC) in prescription amount was weighed, added with 95% ethanol, stirred under heating at 40° C.-50° C., dissolved, then added with the prescription amount of PVP K30, stirred under heating at 40° C.-50° C., dissolved, stirred homogeneously, added with the prescription amount of aerosil, added 95% ethanol to the prescription amount, stirred, to obtain sustained-release coating solution.

500 g of the above topiramate drug-loaded pellet cores was separately weighed and placed in a fluidized bed bottom spray coating pan, the inlet air temperature was set as 40-45° C. (to keep pan internal temperature at 30-35° C.); inlet air pressure was 0.35 bar; atomization pressure was 1.5 bar; solution spray rate was 3-12 g/min. The sustained-release coating solutions of the 3 prescriptions were sprayed on surface of drug-loaded pellets with different corresponding particle diameters in manner of bottom spray under stirring when the drug-loaded pellets were in fluidization state, to obtain sustained-release pellets of topiramate with different particle diameters, the weight increment of coating was 6%. Via calculation, the adhesion degrees of pellets were 1.9, 2.0, 1.7%, respectively. The measurement results of release rates were shown in Table 10. The results showed that the sustained-release features of the preparations would not be influenced when the drug layer and sustained release layer were added with an amount of other adjuvants, such as surfactants, solubilizers, anti-sticking agents.

TABLE 10

Measurement results of drug release rates of prescriptions 14-16

| Prescription | Release rate (%) | | | | |
|---|---|---|---|---|---|
| | 1 h | 4 h | 8 h | 16 h | 20 h |
| Prescription 14 | 9.60 | 39.6 | 66.3 | 95.7 | 97.1 |
| Prescription 15 | 9.4 | 36.6 | 65.3 | 96.8 | 98.8 |
| Prescription 16 | 9.2 | 37.8 | 68.2 | 96.9 | 99.7 |

Example 21

Preparation of Sustained-Release Pellets of Topiramate 500 g of the topiramate drug-loaded pellet cores prepared according to Prescription 1 in Example 11, which drug layer contained binding agent HPMC, was weighed, and placed in a fluidized bed bottom spray coating pan. 720 ml of 95% ethanol was used to prepare a sustained-release coating solution containing ethyl cellulose and PVP K30 respectively in amount of 30 g and 10 g. The inlet air temperature was set as 40-45° C. (to keep pan internal temperature at 30-35° C.); inlet air pressure was 0.35 bar; atomization pressure was 1.5 bar; solution spray rate was 3-12 g/min. The sustained-release coating solution was sprayed on surface of drug-loaded pellets in manner of bottom spray when the drug-loaded pellets were in fluidization state, to obtain sustained-release pellets of topiramate with a drug layer containing binding agent HPMC, the weight increment of coating was 6.86.

Example 22

Preparation of Sustained-Release Pellets of Topiramate

| | Prescription | |
|---|---|---|
| Name of ingredients | Usage amount per 10000 preparation units (g) | Usage amount ratio (%)(w/w) |
| Topiramate | 230 | 36.85 |
| Microcrystalline cellulose (Avicel ® PH102) | 324.9 | 52.05 |
| Methyl cellulose (Methocel ™A15LV) | 20.1 | 3.22 |
| Ethyl cellulose | 34.14 | 5.47 |
| Povidone (Povidone K30) | 14.92 | 2.39 |

Preparation Method:

Topiramate as main drug and microcrystalline cellulose as filling agent in the prescription amounts passed through sieve and mixed homogeneously; 70% ethanol was used to dissolve methyl cellulose (MethocelTMA15LV) to obtain a solution as binding agent with a suitable concentration, and then used to form soft material; the soft material was placed in an extruder using a certain mesh sieve and extrusion rate to extrude rod like granules; the extruded granules were placed in a spheronizator and spheronized under certain spheronization speed for 3-5 min, the obtained pellets were dried in 40° C. oven for 2 h to obtain topiramate drug-loaded pellet cores.

The prescription amounts of ethyl cellulose and Povidone (Povidone K30) were weighed, added with 820 ml of 95% ethanol, stirred and dissolved to form a sustained-release coating solution. The above prepared topiramate drug-loaded pellet cores were placed in a fluidized bed bottom spray coating pan, the inlet air temperature was set as 40-45° C. (to keep pan internal temperature at 30-35° C.); inlet air pressure was 0.35 bar; atomization pressure was 1.5 bar; solution spray rate was 1-3 g/min. The sustained-release coating solutions was sprayed on surface of drug-loaded pellet cores when the drug-loaded pellets were in fluidization state, to obtain sustained-release pellets of topiramate, the weight increment of coating was 6.68%.

Example 23

Studying on Stability of Topiramate Pellets

The sustained-release pellets of topiramate prepared in Example 21 and Example 22, and the first Batch of sustained-release pellets of topiramate prepared in Example 16 were separately placed nakedly in sealed dryer with saturated NaCl solution, then the dryer was placed in high temperature 60° C. oven, acceleration conditions of high temperature and high humidity (60° C., RH75%) were set in the meantime, and samples were taken on $0^{th}$, $5^{th}$ and $10^{th}$ day.

The content of pellet sample was poured out, placed in 10 mL volumetric flask, dissolved with a suitable amount of methanol under ultrasonic waves, then diluted with water in 5 times volume to reach scale, so that the concentration of main drug was about 5 mg/ml, 0.45 μm organic microfiltration membrane was used for filtration, primary filtrate was discarded, the subsequent filtrate were used as test solutions. High performance liquid chromatography (Appendix V D, Part II of Chinese Pharmacopoeia, 2010 Edition) was used, octylsilane-bonded silica gel was used as packing agent, column temperature was 35° C., 40% methanol was mobile phase, differential refractive detector was used, flow rate was 1.5 ml per minute. 200 μl of the test solution was taken, injected in liquid chromatograph, chromatogram was recorded until 3 times the time period of main peak retention time, if the test solution had peaks of impurities, the total content of impurities was calculated by peak area normalization method, and the results were shown in Table 11. It could be seen that the sustained release composition of topiramate (the coating type drug-loaded pellet cores in which the topiramate drug layer was free of binding agent, sample of Example 16) as disclosed in the present invention had stability superior to the matrix type drug-loaded pellet cores (sample of Example 22) and the coating type drug-loaded pellet cores (sample of Example 21) which all had topiramate drug layer containing a binding agent.

TABLE 11

Results of stability of sustained-release pellets of topiramate

| | Degradation products (relevant substances) (%) | | |
|---|---|---|---|
| Sample of stability | $0^{th}$ day | $5^{th}$ day | $10^{th}$ day |
| Sample of Example 20 | 0.15 | 0.37 | 0.55 |
| Sample of Example 21 | 0.15 | 0.38 | 0.57 |
| Sample of Example 16 | 0.15 | 0.21 | 0.28 |

What is claimed is:

1. A composition comprising synephrine or salt thereof, and topiramate, optionally, further comprising a pharmaceutically acceptable adjuvant, wherein the composition is formulated to provide a daily dose of 20 mg to 100 mg of topiramate and 5 mg to 20 mg of synephrine or salt thereof, wherein the synephrine or salt thereof is formulated as a rapid-release preparation characterized by an in vitro dissolution rate of at least 80% of the synephrine or salt thereof within 60 minutes.

2. A method for weight loss or treatment of obesity of an individual in need thereof, the method comprising administering to the individual synephrine or salt thereof and topiramate with a daily dose of 20 mg to 100 mg of topiramate and 5 mg to 20 mg of synephrine or salt thereof, wherein the synephrine or salt thereof is formulated as a rapid-release preparation characterized by an in vitro dissolution rate of at least 80% of the synephrine or salt thereof within 60 minutes.

3. The method according to claim 2, wherein the synephrine or salt thereof and topiramate are simultaneously or separately administered to the individual.

4. The method of claim 2, wherein the topiramate is a sustained-release preparation.

5. The composition of claim 1, formulated in dosage form of capsules, tablets or granules.

6. The composition of claim 1, formulated to provide a daily dose of 5 mg, 10 mg or 20 mg of Synephrine or salt thereof, and a daily dose of 23 mg, 46 mg or 92 mg of topiramate.

7. A sustained-release pellet, consisting of the following 3 parts: a) a blank pellet core; b) an active drug layer, wherein the active drug layer is free of a binding agent selected from the consisting of starch slurry, syrup, polyvinylpyrrolidone, methyl cellulose (MC), ethyl cellulose (EC), highly-substituted hydroxypropyl cellulose (H-HPC), hydroxypropyl methyl cellulose (HPMC), sodium carboxymethyl cellulose, gelatin, Arabic gum, and a mixture thereof; and c) a sustained-release coating layer,
wherein, the active drug layer is located on surface of the blank pellet core, the sustained-release coating layer covers the external surface of the active drug layer,
wherein the active drug is topiramate.

8. A method for preparing the sustained-release pellet of claim 7, the method comprising:
a) providing topiramate to perform drug-loading and coating a blank pellet core to obtain a drug-loaded pellet;
b) coating the drug-loaded pellet obtained in step a) with a sustained-release coating layer;
wherein the active drug layer further comprises other pharmaceutically acceptable adjuvants;
wherein the active drug and optional adjuvants of step a) is dissolved with a suitable amount of solvent to form a drug solution, and the blank pellet core is coated with the drug solution;
wherein in step b), a sustained-release coating material and other adjuvants of the sustained-release coating layer are dissolved in a solvent, and used for sustained-release coating the drug-loaded pellet obtained in step a);
wherein the solvent is water, ethanol, acetone, propylene glycol, chloroform or a mixture thereof.

9. The method of claim 4, wherein the topiramate is a sustained-release pellet, wherein the sustained-release pellet of topiramate consists of the following 3 parts: a) a blank pellet core for the sustained-release pellet; b) an active drug layer comprising topiramate, wherein the drug layer is free of a binding agent selected from the group consisting of starch slurry, syrup, polyvinylpyrrolidone, methyl cellulose (MC), ethyl cellulose (EC), highly-substituted hydroxypropyl cellulose (H-HPC), hydroxypropyl methyl cellulose (HPMC), sodium carboxymethyl cellulose, gelatin, Arabic gum, and a mixture thereof; and c) a sustained-release coating layer, wherein the active drug layer is located on the surface of the blank pellet core, and the sustained-release coating layer covers the external surface of the active drug layer;
wherein the sustained-release coating layer comprises a sustained-release coating material;
wherein the sustained-release coating layer further comprises a plasticizer, a pore-forming agent, an anti-sticking agent, a coloring agent, a light-screening agent, a flavoring agent, or a sweetening agent.

10. The method of claim 9, wherein the synephrine or salt thereof is a rapid release pellet,
wherein the rapid-release pellet of synephrine or salt thereof comprises active drug synephrine or salt thereof, a filling agent, and a binding agent;
wherein the rapid-release pellet of synephrine or salt thereof consists of 2 following parts: a) a blank pellet core for the rapid-release pellet; b) and an active drug layer comprising synephrine or salt thereof, wherein the active drug layer is located on surface of the blank pellet core;
wherein the blank pellet core for either the rapid-release pellet or the sustained-release pellet has a particle diameter of 150 μm-1500 μm.

11. The method of claim 9, wherein the sustained-release coating material comprises a combination of ethyl cellulose and Eudragit NE 30D.

12. The method of claim 9, wherein the sustained-release coating material comprises ethyl cellulose.

13. The method of claim 9, wherein the plasticizer comprises glycerol triacetate.

14. The method of claim 10, wherein the blank pellet core for either the rapid-release pellet or the sustained-release pellet has a particle diameter of 610 μm-750 μm.

15. The composition of claim 1, formulated to provide a daily dose of 5 mg to 20 mg of the synephrine or salt thereof and a daily dose of 23 mg to 92 mg of the topiramate.

16. The method of claim 8, wherein the solvent is a combination of 50% to 95% ethanol-water solution.

17. The method of claim 9, wherein the sustained coating layer comprises ethyl cellulose and polyvinylpyrrolidone (PVP) K30.

18. The method of claim 17, wherein the usage amount ratio of ethyl cellulose to PVP K30 is 1:0.20-1:0.45 and the weight of the sustained-release coating layer is 5% to 15% of the sustained-release pellet.

19. The method of claim 18, wherein the usage amount ratio of ethyl cellulose to PVP K30 is 1:0.3-1:0.35.

20. The method of claim 18, wherein the weight of the sustained-release coating layer is 6% to 8% of the sustained-release pellet.

21. A method for preparing the sustained-release pellet of claim 7, the method comprising:
a) providing topiramate and optional other adjuvants, adding with a suitable amount of solvent, heating and dissolving under stirring to form a drug solution, providing a blank pellet core and placing in a fluidized bed coating pan for one-step pelletization, performing drug-loading and coating with the drug solution under stirring;

b) dissolving a sustained-release coating material and other adjuvants of the sustained-release coating layer in a solvent, heating and dissolving under stirring, mixing homogeneously, passing through a sieve, to obtain a sustained-release coating solution; and c) taking the drug-loaded pellet, spraying the sustained-release coating solution on surface of the drug-loaded pellet in a fluidized bed, to obtain the sustained-release pellet of topiramate.

22. The composition of claim 1, wherein the synephrine or salt thereof is synephrine hydrochloride.

23. The method of claim 3, wherein the synephrine or salt thereof is administered first, then the topiramate is administered after an interval of time; or the topiramate is administered first, then the synephrine or salt thereof is administered after an interval of time, wherein the interval of time is 0-24 h.

24. The method of claim 9, wherein the drug layer of sustained-release pellet of topiramate consists of topiramate.

25. The method of claim 2, wherein the topiramate is a sustained-release pellet consists of the following 3 parts: a) a blank pellet core for the sustained-release pellet; b) an active drug layer comprising topiramate, wherein the drug layer is free of a binding agent selected from the group consisting of starch slurry, syrup, polyvinylpyrrolidone, methyl cellulose (MC), ethyl cellulose (EC), highly-substituted hydroxypropyl cellulose (H-HPC), hydroxypropyl methyl cellulose (HPMC), sodium carboxymethyl cellulose, gelatin, Arabic gum, and a mixture thereof; and c) a sustained-release coating layer.

* * * * *